United States Patent [19]
Wythes et al.

[11] Patent Number: 6,166,011
[45] Date of Patent: Dec. 26, 2000

[54] FKBP INHIBITORS

[75] Inventors: Martin J. Wythes, New London, Conn.; Michael J. Palmer, County of Kent, United Kingdom; Mark I. Kemp, County of Kent, United Kingdom; Malcolm C. MacKenny, County of Kent, United Kingdom; Robert J. Maguire, County of Kent, United Kingdom; James F. Blake, Jr., Mystic, Conn.

[73] Assignee: Pfizer Inc, New York, N.Y.

[21] Appl. No.: 09/354,193

[22] Filed: Jul. 15, 1999

[30] Foreign Application Priority Data

Jul. 20, 1998 [GB] United Kingdom .................. 9815696

[51] Int. Cl.⁷ .................................................. A61K 31/535
[52] U.S. Cl. ...................... 514/233.8; 544/130; 544/364; 546/187; 546/197
[58] Field of Search ............................ 544/130; 546/187; 514/233.8

[56] References Cited

U.S. PATENT DOCUMENTS 5,721,256   2/1998   Hamilton et al. .

FOREIGN PATENT DOCUMENTS 0295656   12/1988   European Pat. Off. .
0657451   6/1995   European Pat. Off. .
980256   7/1998   South Africa .
WO9813355   4/1998   WIPO .

*Primary Examiner*—Robert W. Ramsuer
*Attorney, Agent, or Firm*—Peter C. Richardson; Paul H. Ginsburg; Kristina L. Konstas

[57] ABSTRACT

Compounds of formula (I), their salts and solvates, wherein the substituents are as described herein, are FKBP inhibitors.

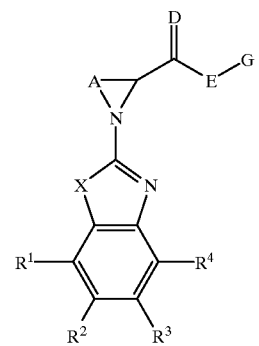

(I)

29 Claims, No Drawings

FKBP INHIBITORS

This application claims the benefit under 35 U.S.C. 119 of Great Britain Patent Application 9815696.1, entitled "Heterocycles", filed Jul. 20, 1998.

This invention relates to 1-heteroaryl-pyrrolidine, -piperidine and -homopiperidine derivatives and to process for the preparation of, intermediates used in the preparation of, composition containing and the uses of, such derivatives.

It has been reported that the immunosuppressant FK-506 promotes neurite outgrowth in vitro in neuronal cell line and culture models (see Lyons et al, *Pro. Natl. Acad. Sci.*, 1994, 91, 3191–95 and Snyder et al, *Nature Medicine*, 1995, 1, 32–37). International Patent Application publication nos. WO 96/40140, WO 96/40633 and WO 97/16190 disclose compounds that have neurotrophic activity but which lack inhibitory action at the protein phosphatase calcineurin and therefore which have no immunosuppressive activity.

It has been suggested in International Patent Applications publication numbers WO 96/40140 and WO 96/40633 that the neurotrophic effect of these compounds is mediated, at least in part, by a high affinity interaction with the FK-506 binding proteins, such as FKBP-12 or FKBP-52. However, the mechanism by which this interaction with FKBP-type immunophilins results in a neurotrophic effect is at present unknown. The range of neurotrophic activity that can be realised through this neurotrophic/non-immunosuppressant class of compounds has been explored and it has been found that axon regeneration can be promoted after facial nerve crush and sciatic nerve crush in the rat. It has also been observed that the functional regeneration of dopamine neurons damaged with the toxin MPTP was promoted by the compounds disclosed therein in mice. Additionally, it was reported that restoration of striatal innervation in the rat was promoted by the compounds disclosed therein following 6-hydroxydopamine lesioning of dopaminergic neurons (see Hamilton & Steiner, *Current Pharmaceutical Design*, 1997, 3, 405–428).

International Patent Application publication numbers WO 98/00278, WO 98/13343, WO 98/13355, WO 98/20891, WO 98/20892 and WO 98/20893 describes various neurotrophic pyrrolidine, piperidine and homopiperidine derivatives having an acyl, amide, oxalyl, or similar linking group, at the 1-position of the heterocycle.

U.S. Pat. No. 5,721,256 describes various pyrrolidine piperidine and homopiperidine derivatives having an $SO_2$ linking group at the 1-position of the heterocycle, as having affinity for rotamase enzymes.

European Patent Application publication number 0 657 451 A2 generically discloses a number of 2-(1-pyrrolidino)-benzoxazoles as leukotriene biosynthesis inhibitors, and specifically discloses methyl 1-(5-chloro-2-benzoxazolyl) proline.

It has now been found that the presently-disclosed substances are neurotrophic agents which have an affinity for FKBP-type immunophilins. In particular, they are potent inhibitors of the enzyme activity and especially of the cis-trans prolyl isomerase (rotamase) activity of FKBP-type immunophilins, particularly the immunophilins FKBP-12 and FKBP-52. The present substances do not significantly inhibit the protein phosphate calcineurin and therefore lack any significant immunosuppressive activity.

The present substances moderate neuronal degeneration and promote neuronal regeneration and outgrowth and as such can be used for treating neurological disorders arising from neurodegenerative diseases or other disorders involving nerve damage. The neurological disorders that may be treated include senile dementia (Alzheimer's disease) and other dementias, amyotrophic lateral sclerosis and other forms of motor neurone disease, Parkinson's disease, Huntington's disease, neurological deficits associated with stroke, all forms of degenerative disease affecting the central or peripheral nervous system (e.g. cerebellar-brainstem atrophies, snydromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases.

Preferably, the present substances can be used for treating senile dementia (Alzheimer's disease) or another dementia, amyotrophic lateral sclerosis or another form of motor neurone disease, Parkinson's disease, Huntingdon's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus.

The substances of the present invention are compounds of the formula (I):

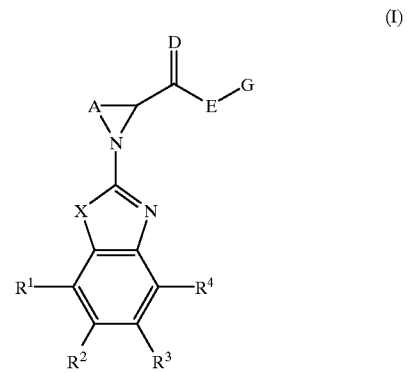

or a pharmaceutically acceptable salt, or solvate of either entity, wherein:

X is O, S, NH or N($C_{1-6}$ alkyl);

$R^1$, $R^2$, $R^3$ and $R^4$ are each independently H, OH, OCO($C_{1-6}$ alkyl), $CO_2$($C_{1-4}$ alkyl), $CONH_2$, CONH($C_{1-6}$ alkyl), CON($C_{1-6}$ alkyl)$_2$, halo, $C_{3-7}$ cycloalkyl, $C_{3-7}$ cycloalkyloxy, $C_{2-6}$ alkenyl, aryl$^1$, $C_{1-6}$ alkyl optionally substituted by one or more substituents selected from halo and $C_{3-7}$ cycloalkyl, and $C_{1-6}$ alkoxy optionally substituted by one or more substituents selected from fluoro and $C_{3-7}$ cycloalkyl;

A is unbranched $C_{3-5}$ alkylene optionally substituted by up to three $C_{1-6}$ alkyl groups;

D is O or S;

E is O, S, NH, N($C_{1-6}$ alkyl) or $CR^{11}R^{12}$;

G is $C_{1-14}$ alkyl or $C_{2-14}$ alkenyl, each of which is optionally substituted by one or more substituents independently selected from halo, aryl, $C_{1-4}$ alkoxy, cycloalk, het and $NR^5R^6$, $R^5$ and $R^6$ are either each independently H or $C_{1-6}$ alkyl, or are taken together to form, with the nitrogen atom to which they are attached, a 4 to 7-membered heterocyclic ring optionally containing another hetero-moiety selected from $NR^7$, O and $S(O)_p$, and which 4 to 7-membered heterocyclic ring is optionally substituted by up to 3 substituents independently selected from $C_{1-6}$ alkyl and $C_{1-6}$ alkoxy;

$R^7$ is H, $C_{1-6}$ alkyl, $C_{2-6}$ alkenyl, $COR^8$, $SO_2R^8$, $CONR^9R^{10}$, $CO_2R^8$ or $SO_2NR^9R^{10}$;

$R^8$ is $C_{3-7}$ cycloalkyl, $C_{2-6}$ alkenyl, aryl$^1$, or $C_{1-6}$ alkyl optionally substituted by $C_{3-7}$ cycloalkyl or aryl$^1$;

$R^9$ and $R^{10}$ are each independently H, $C_{2-6}$ alkenyl, $C_{3-7}$ cycloalkyl, or $C_{1-6}$ alkyl optionally substituted by $C_{3-7}$ cycloalkyl or aryl;

$R^{11}$ and $R^{12}$ are each independently H, aryl, $C_{2-8}$ alkenyl or $C_{1-8}$ alkyl, wherein said $C_{2-8}$ alkenyl and $C_{1-8}$ alkyl groups are optionally substituted by one or more substituents independently selected from halo, $NO_2$, $C_{1-6}$ alkenyl, cycloalk, OH, $C_{1-6}$ alkoxy, $C_{2-6}$ alkenyloxy, phenyloxy, benzyloxy, $NH_2$, aryl and het;

p is 0, 1 or 2;

wherein "aryl" means phenyl or naphthyl, each of which is optionally substituted by up to 3 substituents independently selected from $C_{1-6}$ alkyl optionally substituted by one or more halo or $C_{3-7}$ cycloalkyl groups, $C_{2-6}$ alkenyl, $C_{1-6}$ alkoxy, $C_{2-6}$ alkenyloxy, OH, halo, $NO_2$, phenyloxy, benzyloxy, phenyl and $NH_2$;

"aryl" means phenyl, naphthyl or benzyl, each of which is optionally substituted by 1 or 2 substituents independently selected from $C_{1-6}$ alkyl optionally substituted by one or more halo or $C_{3-7}$ cycloalkyl groups, $C_{1-6}$ alkoxy and halo;

"cycloalk" is $C_{3-8}$ cycloalkyl optionally substituted by up to 3 substituents independently selected from $C_{2-6}$ alkenyl, $C_{1-6}$ alkoxy, $C_{2-6}$ alkenyloxy, OH, halo, and $C_{1-6}$ alkyl optionally substituted by one or more halo;

and "het" means a 5- or 6-membered monocyclic, or 8-, or 9- or 10-membered bicyclic heterocycle containing 1 to 3 heteroatoms independently selected from O, N and S, which is optionally substituted by up to 3 substituents independently selected from $C_{1-6}$ alkyl optionally substituted by one or more halo or $C_{3-7}$ cycloalkyl groups, $C_{2-6}$ alkenyl, $C_{1-6}$ alkoxy, $C_{2-6}$ alkenyloxy, OH, halo, $NO_2$, phenyloxy, benzyloxy and $NH_2$;

with the proviso that the compound is not methyl 1-(5-chloro-2-benzoxazolyl)proline.

Throughout the above definitions, "halo" means fluoro, chloro, bromo or iodo. Alkyl, alkoxy, alkenyl, alkylene and alkenylene groups, except where indicated, can be unbranched- or branched-chain, where the number of carbon atoms allows.

It is to be appreciated herein that where X is NH, in certain conditions the NH proton can be mobile and can reside on the other nitrogen in the benzimidazole ring, viz. formula (IA) below:

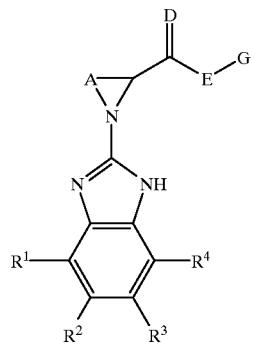

(IA)

It is to be understood that all such compounds of formula (IA) are included in the scope of the compounds of formula (I) as tautomerss thereof.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts for example Berge et al, *J. Pharm. Sci.*, 1977, 66, 1–19.

The pharmaceutically acceptable solvates of the compounds of the formula (I) include the hydrates thereof.

Also included within the present scope of the substances of the invention are polymorphs and radiolabelled derivatives thereof.

A compound of the formula (I) contains one or more asymmetric carbon atoms and therefore exists in two or more stereoisomeric forms. The present invention includes the individual stereoisomers of the compounds of the formula (I) and, where appropriate, the individual tautomeric forms thereof, together with mixtures thereof.

Certain of the compounds of formula (I) can exist as geometric isomers. The present invention includes the individual geometric isomers of the compounds of the formula (I), together with mixtures thereof.

Separation of diastereoisomers and geometric isomers may be achieved by conventional techniques, e.g. by fractional crystallisation, chromatography or H.P.L.C. of a mixture of isomers of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Certain of the compounds of formula (I) can exist as tautomers. It is to be understood that the invention encompasses all individual tautomers of the compounds of formula (I), together with mixtures thereof.

Preferably X is O or NH.

Preferably at least two of $R^1$, $R^2$, $R^3$ and $R^4$ are H.

Preferably $R^1$ H, halo or $CO_2(C_{1-6}$ alkyl). More preferably $R^1$ H or $CO_2CH_3$.

Preferably $R^2$ is H, halo, $C_{3-7}$ cycloalkyl, $C_{3-7}$ cycloalkyloxy, $C_{2-6}$ alkenyl, $C_{1-6}$ alkyl optionally substituted by one or more substituents selected from halo and $C_{3-7}$ cycloalkyl, or $C_{1-6}$ alkoxy optionally substituted by one or more substituents selected from fluoro and $C_{3-7}$ cycloalkyl.

More preferably $R^2$ is H, halo, $C_{1-6}$ alkyl optionally substituted by one or more substituents selected from halo and $C_{3-7}$ cycloalkyl, or $C_{1-6}$ alkoxy optionally substituted by one or more $C_{3-7}$ cycloalkyl groups.

Yet more preferably $R^2$ is H, halo, $C_{1-4}$ alkyl optionally substituted by one or more halo, or $C_{1-4}$ alkoxy.

Even more preferably $R^2$ is H, F, I, Br, Cl, $CH_3$, $C_2H_5$, $CH_2CH(CH_3)_2$, $CF_3$, $OCH_3$ or $OCH(CH_3)_2$.

Most preferably $R^2$ is H, F, Cl, Br, I or $CF_3$.

Preferably $R^3$ is H, halo, $C_{3-7}$ cycloalkyl, $C_{3-7}$ cycloalkyloxy, $C_{2-6}$ alkenyl, $C_{1-6}$ alkyl optionally substituted by one or more substituents selected from halo and $C_{3-7}$ cycloalkyl, or $C_{1-6}$ alkoxy optionally substituted by one or more substituents selected from fluoro and $C_{3-7}$ cycloalkyl.

More preferably $R^3$ is H, halo, $C_{1-6}$ alkyl optionally substituted by one or more substituents selected from halo and $C_{3-7}$ cycloalkyl, or $C_{1-6}$ alkoxy optionally substituted by one or more $C_{3-7}$ cycloalkyl groups.

Yet more preferably $R^3$ is H, halo, $C_{1-4}$ alkyl optionally substituted by one or more halo, or $C_{1-4}$ alkoxy.

Even more preferably $R^3$ is H, F, I, Br, Cl, $CH_3$, $C_2H_5$, $CH_2CH(CH_3)_2$, $CF_3$, $OCH_3$ or $OCH(CH_3)_2$.

Most preferably $R^3$ is H, F, Cl, Br, I or $CF_3$.

When X is O or NH, $R^2$ and $R^3$ are preferably each independently H, halo or $CF_3$.

Preferably $R^4$ is H, halo or $C_{1-6}$ alkyl. More preferably $R^4$ is H or $CH_3$.

Preferably A is unbranched $C_{3-5}$ alkylene optionally substituted by a $C_{1-6}$ alkyl group. More preferably A is unbranched $C_{3-5}$ alkylene. Most preferably A is butylene, i.e. $(CH_2)_4$.

Preferably D is O.

Preferably E is NH or $N(C_{1-6}$ alkyl). Most preferably E is NH.

Preferably G is $C_{1-14}$ alkyl or $C_{2-14}$ alkenyl, each of which is mono- or disubstituted by substituents independently selected from het, aryl, cycloalk or $NR^5R^6$.

More preferably G is $C_{2-4}$ alkyl or $C_{2-4}$ alkenyl, each of which is terminally monosubstituted by $NR^5R^6$.

Yet more preferably G is $C_{2-4}$ alkyl or $C_{2-4}$ alkenyl, each of which is terminally substituted by $NR^5R^6$, where $R^5$ and $R^6$ are either each independently H or $C_{1-6}$ alkyl, or are taken together to form, with the nitrogen atom to which they are attached, a 5 to 7-membered ring optionally containing another hetero-moiety selected from $NR^7$ or O, and which ring is optionally substituted by up to 3 substituents independently selected from $C_{1-6}$ alkyl and $C_{1-6}$ alkoxy, and wherein $R^7$ is H, $C_{1-6}$ alkyl, $COR^8$ or $CONR^9R^{10}$.

Even more preferably G is $(CH_2)_mNR^5R^6$, where m is 2, 3 or 4, and $R^5$ and $R^6$ are either each both H, or are taken together to form, with the nitrogen atom to which they are attached, a 6-membered ring optionally containing another hetero-moiety at the 4-position relative to the ring nitrogen directly attached to the $(CH_2)_m$ moiety, which hetero-moiety is selected from NH, $NCOCH_3$, $NCH_3$, $NCONHCH(CH_3)_2$ or O, and which ring is optionally substituted by up to 2 $CH_3$ substituents on the ring atoms adjacent to the ring nitrogen directly attached to the $(CH_2)_m$ moiety.

Further more preferably, G is $(CH_2)_2NR^5R^6$, where $R^5$ and $R^6$ are both H or are taken together taken together to form, with the nitrogen atom to which they are attached, a 6-membered ring optionally containing another hetero-moiety at the 4-position relative to the ring nitrogen directly attached to the $(CH_2)_m$ moiety, which hetero-moiety is selected from NH, $NCOCH_3$, $NCH_3$, $NCONHCH(CH_3)_2$ or O, and which ring is optionally substituted by up to 2 $CH_3$ substituents on the ring atoms adjacent to the ring nitrogen directly attached to the $(CH_2)_2$ moiety.

Most preferably G is $(CH_2)_2NR^5R^6$, where $NR^5R^6$ is piperidino, morpholino, piperazino,

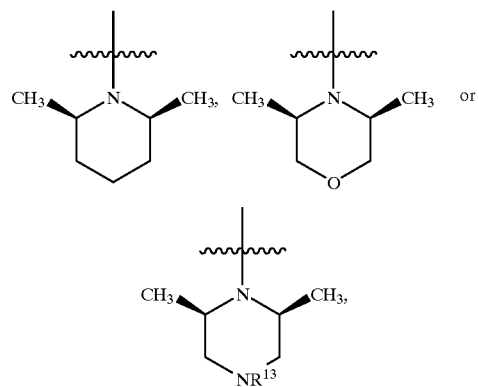

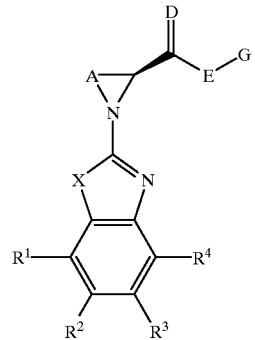

where $R^{13}$ is H, $COCH_3$, $CH_3$, or $CONHCH(CH_3)_2$.

Preferably the compounds have the stereochemistry shown in formula (IB) below.

(IB)

A preferred group of substances are those where the substituents X, A, D, E, G, $R^1$, $R^2$, $R^3$ and $R^4$ have the values found in the Examples below, and the stereochemistry is as shown above in formula (IB).

The most preferred group of substances are the compounds of the Examples below and their salts and solvates.

Particularly preferred substances are the compounds of Examples 3, 10, 11, 12, 16, 17, 18, 19, 20, 22, 27 and 31, and the salts and solvates thereof.

The compounds of the formula (I) can be prepared by a number of methods using conventional procedures such as by the following illustrative methods, and suitable adaptation thereof. Such methods are a further aspect of the invention.

Unless otherwise specified below, the substituents are as defined for the compounds of formula (I) above.

Method 1

All the compounds of formula (I) can be made via reaction of a compound of the formula (II) (including regioisomers thereof (IIA) where appropriate) below where $X^1$ is O, S, N($C_{1-6}$ alkyl) or N(APG), where "APG" is an amino-protecting group which can be readily removed to give the corresponding NH compound, and $L^1$ is a suitable leaving moiety such as Cl, Br, I, SH, $SCH_3$, $SO_2CH_3$, $SO_2CF_3$, $OSO_2CH_3$ or $OSO_2CF_3$, with a compound of formula (III) below.

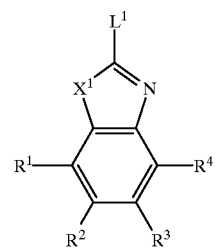

(II)

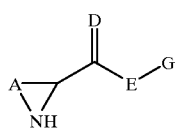

(III)

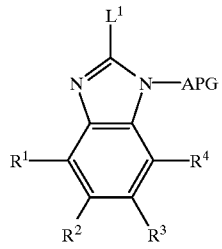

(IIA)

Suitable amino-protecting groups are well-known to the skilled chemist and are exemplified in "Protecting Groups in Organic Synthesis" by T. W. Greene and P. G. M. Wuts, John Wiley & Sons Inc., 1991, herein incorporated by reference. Preferably the amino-protecting group is the t-butyloxycarbonyl ("Boc") group, which can be readily removed either in situ during the course of the reaction between (II) and (III) above, or by later treatment with trifluoroacetic acid (TFA), in a suitable solvent such as dichloromethane.

Typically the reaction is carried out by heating the substrates (II) (including regioisomers (IIA) thereof where appropriate) and (III) together in a suitable organic solvent such as dimethylacetamide, to a temperature in the range 25–200° C., preferably around 80° C., optionally in the presence of a base such as triethylamine or diisopropylethylamine, also optionally in the presence of a metal such as copper.

Compounds of formulae (II) (including regioisomers (IIA) thereof where appropriate) and (III) are available by conventional methods such as those exemplified in the Preparations below.

Method 2

Compounds of the formula (I) where X is O or S, D is O and E is O, S, NH or N($C_{1-6}$ alkyl), can be prepared by reaction of a compound of the formula (IV):

(IV)

where X is O or S, and $L^2$ is a suitable leaving group such as azide, mesylate, tosylate, OH, Cl, Br, I, etc., including where the $COL^2$ moiety is a suitable activated ester, with a compound of formula G-E-H, or salt thereof. Examples of such activated esters can be derived from the parent acid (IV; $L^2$ is OH), for example by reaction with a hydroxybenzotriazole-type reagent such as 1-hydroxybenzotriazole, and a carbodiimide reagent such as 1-(3-dimethylaminopropyl)-3-ethylcarbodiimide. These types of acid-activating reagents can be used alone or in combination. Examples of hydroxybenzotriazole based reagents which can be used by themselves are benzotriazol-1-yloxytris(dimethylamino)-phosphonium hexafluorophosphate and O-(1H-benzotriqzol-1-yl)-N,N,N',N'-tetramethyluronium tetrafluoroborate. Further examples of $L^2$ include the moieties derived from reaction of (IV, $L^2$ is OH) with pentafluorophenol and N-hydroxysuccinimide. Similarly, $L^2$ moieties can be used which make compounds of formula (IV) a mixed anhydride and examples include the compounds derived from reaction of compounds of formula (IV; $L^2$ is OH) with reagents such as isobutylchloroformate and bis(2-oxo-3-oxazolidinyl)phosphinic chloride. Additionally, $L^2$ can be imidazolyl, such compounds being derived from reaction of compounds of formula (IV; $L^2$ is OH), with N,N'-carbonyldiimidazole.

The reaction of compounds of formula (IV) with compounds of formula G-E-H is suitably carried out in a suitable solvent in the presence of an optional base, such as N-methylmorpholine.

Additionally, compounds of the formula (I), where X is O or S, D is O and E is O, NH or N($C_{1-6}$ alkyl), may be prepared by directly heating together compounds of the formula (IV) (including tautomers thereof where appropriate), for example where $L^2$ is OH, with compounds of the formula G-E-H, where E is O, NH or N($C_{1-6}$ alkyl), optionally in the presence of a catalyst, such as a suitable acid or base, and optionally in an appropriate solvent.

Additionally, in an analogous synthesis, compounds of formula (I) where X is NH can be made via reaction of a compound of formula (IVA) or (IVB):

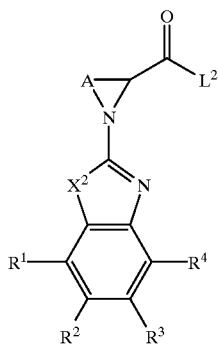

(IVA)

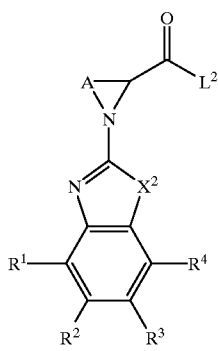

(IVB)

where $X^2$ is N-APG, where APG is defined as for Method 1 above.

Compounds of formulae (IVA) and (IVB) where $X^2$ is N-Boc and $L^2$ is OH can in certain circumstances, for example in the presence of certain dehydrating systems such as in a hydroxybenzotriazole/1-(3-dimethylamino)-3-ethylcarbodiimide hydrochloride/N-methylmorpholine in a suitable organic solvent such as dichloromethane, form compounds of formulae (IVC) and (IVD):

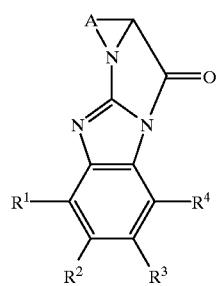

(IVC)

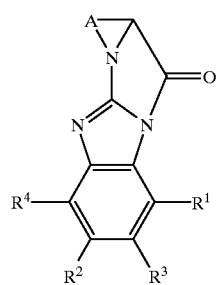

(IVD)

which may be stable and isolatable.

Compounds of formula (IV) (including tautomers thereof where appropriate) may be prepared by standard methods, such as that outlined in the Preparation below, and suitable variation thereof.

Compounds of formula G-E-H are commercially available or are otherwise available via conventional routes, such as are described in the Preparation below.

Method 3

Compounds of the formula (I) where E is $CR^{11}R^{12}$ can be prepared by reaction of a compound of the formula (IV) (including tautomers thereof where appropriate) as defined above, with an organomettalic species, $M_nCR^{11}R^{12}G$, where n is 1 is less, depending on the valence of the metallic species M. M can be a single metal or a combination of metals, optionally with other ligands such as halides (e.g. Grignard-type reagents). An example of this type of reaction is where $L^2$ is a halide, M is CuLi and n is 0.5. This type of reaction is described in "Advanced Organic Chemistry" by J. March, 3rd edition, Wiley Interscience in sections 1–106 and 0–107 and the references therein, herein incorporated by reference.

Method 4

Compounds of formula (I) where D is S (including tautomers thereof where appropriate) can be made from the corresponding compound of formula (I) where D is O (including tautomers thereof where appropriate) by reaction with a sulphur nucleophile such as those mentioned in "Advanced Organic Chemistry" by J. March, Wiley-Interscience, 1985, section 6–11, and the references therein, herein incorporated by reference.

A suitable reagent for carrying out such a transformation is 2,4-bis(4-methoxyphenyl)-1,3,2,4-dithiadiphosphetane-2,4-disulphide (Lawesson's reagent). For a review of this reagent and reaction, see for instance Pederson, et al, *Bull. Chim. Soc. Belges* 87, 223 (1978).

Method 5

Compounds of the formula (I) are available via reaction of compounds of formula (V) and (VI):

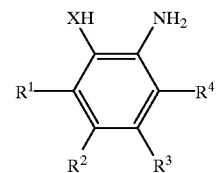

(V)

(VI)

wherein $L^3$ is a suitable leaving group such as Cl, Br, or I. The reaction is suitably carried out in the presence of an additional base such as triethylamine, and in a suitable aprotic organic solvent such as dichloromethane.

The reaction is some circumstances, i.e. specific substituents, solvents, bases, reaction conditions, etc., will proceed directly to give the compound of formula (I). In other circumstances the formation may proceed in a step-wise manner via intermediates of formulae (VII) or (VIII), or salts thereof:

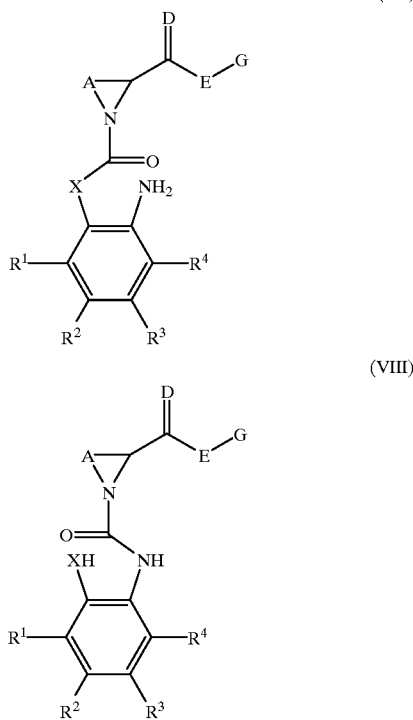

which may be stable and isolatable.

Compounds of formulae (V) and (VI) are available commercially or via standard methods known in the art, or suitable adaptation thereof.

Certain of the substances of the invention may be interconverted into other substances of the invention by conventional functional group interconversion methods.

It will be appreciated that all the substances of the invention are available via methods known in the art and the methods outlined and exemplified herein and suitable adaptation thereof using methods known in the art. The skilled chemist will exercise his skill and judgement as to any necessary adaptation, for instance in the choice of reagents, conditions, compatability of substrates and reagents with desired reaction, order of reaction steps, protection/ deprotection, further reactions, etc.

It will be apparent to those skilled in the art that sensitive functional groups may need to be protected and deprotected during the synthesis of substances of the invention. These steps may be achieved by conventional techniques, for example as described in "Protective Groups in Organic Synthesis" by T. W. Greene and P. G. M. Wuts, John Wiley & Sons Inc., 1991.

Some of the reaction steps outlined herein could result in racemisation at certain sensitive stereochemical centres, if present. The compound with the desired stereochemistry may be made for example by subsequent resolution using conventional methods such as by chiral HPLC, or by instead carrying out the relevant transformation in a manner which does not lead to racemisation, foe example by use of a chiral auxiliary in the reactant.

All of the above reactions and the preparations of novel starting material used in the preceeding methods are conventional and appropriate reagents and reaction conditions for their performance or preparation as well as procedures for isolating the desired products will be well-known to those skilled in the art with reference to literature precedents and the Examples and Preparations herein.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The affinity of the compounds of the formula (I) for FKBP-12 can be determined in vitro in a coupled colorimetric PPIase assay using similar procedures to published methods (e.g. see Kofron, J. L., et al., *Biochemistry*, 1991, 30, 6127–6134, Zarnt, T., et al., *Biochem. J.* 1995, 305, 159–164, Holt, D. A., et al., *J. Am. Chem. Soc.*, 1993, 115, 9925–9938). In these methods, the cis-trans isomerisation of a hydrophobic amino acid-proline bond in tetrapeptide substrate (e.g. the phenylalanine-proline bond in N-succinyl-ala-phe-pro-phe-p-nitroanilide [succinyl-AFPF-pNA]) can be determined by monitoring cleavage of pNA from the transPro-containing peptide by an excess of chymotrypsin.

The $IC_{50}$ (the concentration of the compound of the formula (I) producing 50% inhibition) values were determined using the following assay methodology. Assay buffer (2.175 ml) (50 mM 4-(2-hydroxyethyl)-1-piperazineethanesulphonic acid (HEPES), 100 mM NaCl, 1 mM dithiothreitol (DTT), pH 8.0) is equilibrated to 10° C. in a cuvette. 12.5 µl of a solution of the present compound is DMSO, 250 µl of a 60 mg/ml solution of α-chymotrypsin in 1 mM aqueous hydrochloric acid and then 50 µl of a solution of human recombinant FKBP-12 (4.5 µM) in assay buffer are added and mixed. The reaction is initiated by addition of 12.5 µl of a solution of 20 mM succinyl-AFPF-pNA in DMSO. The absorbance at 390 nM is monitored for one minute collecting data every 0.25 second. Data are fitted with a first order rate equation with offset and the rate constant obtained corrected for the rate of uncatalysed isomerisation of the substrate. The rate constant determined at different inhibitor concentrations (10 mM to 100 µM) is expressed as % inhbition of the control rate constant. The $IC_{50}$ is estimated using a non-linear least squares curve fitting routine of the sigmoidal dose response data.

$K_{i,app}$ (the apparent inhibition constant) was determined for the present compounds using the assay procedure described below. Assay buffer (2.175 ml) (50 mM HEPES, 00 mM NaCl, 1 mM DTT, pH 8.0) is equilibrated to 10° C. in a cuvette. 12.5 µl of a solution of the present compound in DMSO, 250 µl of a 60 mg/ml solution of α-chymotrypsin in 1 mM aqueous hydrochloric acid and then 50 µL of a solution of human recombinant FKBP-12 (1.5 µM) in assay buffer are added and mixed. The reaction is initiated by adding 12.5 µl of a solution of anhydrous succinyl-AFPF-pNA (100 µM final concentration) in a 400 mM solution of LiCl in trifluoroethanol. The absorbance at 390 nM is monitored for 3 minutes collecting data every 0.5 second. Data are fitted with a first order rate equation with offset and the initial velocity (v) is calculated from the concentration of cis (re leu-pro-bond)-succinyl-AFPF-pNA at $t_o$ and the first order rate constant at different inhibitor concentrations (I). Data in the form $v_{inch}/v_{control}$ v. [I] are fitted with an equation for reversible tight binding inhibition to generate values for $K_{i,app}$ (see Morrison, J. F. et al, Comments Mol. Cell Biophys., 1985, 2, 347–368). This analysis is used when the $K_{i,app}$ approaches the concentration of FKBP-12 in the assay (30 nM). Dixon analysis (see Dixon, M., Biochem. J., 1953, 55, 170–171) is used for generating values of $K_{i,app}$ for less potent compounds.

The same methodology is used to measure $K_{i,app}$ for FKBP-52, with the following modifications: 40 µl human recombinant FKBP-52 (5.2 µM) is substituted for FKBP-12 and 2.185 ml assay buffer are used in the assay.

The neurite outgrowth promoting activity of the compounds of the formula (I), without proviso, can be determined in explant cultures of embryonic chick dorsal root ganglia. Dorsal root ganglia (DRG) are isolated aseptically according to the method of Bray (see "Culturing Nerve Cells", Ed. G. Banker and K. Goslin, MIT Press, Cambridge, Mass., 1991, p. 119). The individual ganglia were kept in $Ca^{2+/Mg2+}$-free Tyrodes buffer on ice until a number of ganglia had been collected. Individual ganglia were then transferred into collagen-coated 24-well culture plates containing Neurobasal medium plus B27 supplements and incubated at 37° C. in 5% $CO_2$ atmosphere. The test substance was added after allowing 4 hours for the ganglia to attach. The explants were fixed and stained with Coomassie blue after 24 or 48 hours in culture. For each treatment 4 to 6 ganglia were analysed and scored by estimating the extent of neurite outgrowth relative to the diameter of the explant using image analysis. The present substances were tested with and without 10 ng/ml nerve growth factor (NGF) present and compared to outgrowth in the presence of 10 ng/ml nerve growth factor alone.

An alternative system for measuring neurite outgrowth promoting activity of FKBP-12 PPIase inhibitirs is the SH-SY-5Y neuroblastoma model described by Gold, B. G., et al. in Exp. Neurol., 1997, 147(2), 269–278. Cells are maintained in Dulbecco's Modified Eagle's Medium (DMEM) supplemented with 10% foetal calf serum (FCS), 50 U/ml penicillin, 50 μg/ml streptomycin at 37° C. in a 7% $CO_2$ atmosphere. Cells are plated at $1 \times 10^6$ cells per well and treated for 5 days with 400 nM aphidicolin. Cells are then washed and treated with NGF at 10 ng/ml±various compound concentrations for 7 days to determine if the compounds promote neurite outgrowth in the presence of suboptimal NGF concentrations (and/or in the absence of NGF). Neurite outgrowth is determined by using image analysis to measure neurite lengths in 20 random fields.

The neurotrophic activity of the present substances can be evaluated in vivo using the sciatic nerve crush model in rat as a model for peripheral nerve regeneration (see Bridge, P. M., et al., Experimental Neurology, 1994, 127, 284–290, Medinaceli, L., et al., Expl. Neurology, 1982, 77, 634–643, Gold, B. G., et al., Restorative Neurology and Neuroscience, 1994, 6, 287–296), the 1-methyl-4-phenyl-1,2,3,6-tetrahydropyridine (MPTP) and 6-hydroxydopamine models in various species as a model for regeneration in Parkinson's disease (see Mokry, J., Physiol. Res., 1995, 44(3), 143–150) and fimbriafornix lesions as a model for regeneration in Alzheimer's disease (see Cassel, J. C., Duconseille, E., Jeltsch, H. and Will, B., Prog. Neurol., 1997, 51, 663–716).

The substances of the invention can be administered alone but will generally be administered in admixture with a suitable pharmaceutical excipient diluent or carrier selected with regard to the intended route of administration and standard pharmaceutical practice.

For example, the substances of the invention can be administered orally or sublingually in the form of tablets, capsules, ovules, elixirs, solutions or suspensions, which may contain flavouring or colouring agents, for immediate or controlled release applications.

Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, the substances of the invention may be combined with various sweetening or flavouring agents, colouring matter or dyes, with emulsifying and/or suspending agents and with diluents such as water, ethanol, propylene glycol and glycerin, and combinations thereof.

The substances of the invention can also be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the substances of the invention will usually be from 1 μg/kg to 25 mg/kg (in single or divided doses).

Thus tablets or capsules of the may contain from 0.05 mg to 1.0 g of active substance for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are mertited and such are within the scope of this invenion.

The substances of the invention can also be administered intranasally or by inhalation and are conveniently delivered in the form of a dry powder inhaler or an aerosol spray presentation from a pressurised container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a substance of the invention and a suitable powder base such as lactose or starch.

Aerosol or dry powder formulations are preferably arranged so that each metered dose or "puff" contains from 20 μg to 20 mg of a substance of the invention for delivery to the patient. The overall daily dose with an aerosol will be in the range of from 20 μg to 20 mg which may be administered in a single dose or, more usually, in divided doses throughout the day.

Alternatively, the substances of the invention can be administered in the form of a suppository or pessary, or they may be applied topically in the form of a lotion, solution, cream, ointment or dusting powder. The substances of the invention may also be transdermally administered by the use of a skin patch. They may also be administered by the ocular route, particularly for treating neurological disorders of the eye.

For ophthalmic use, the substances can be formulated as micronised suspensions in isotonic, pH adjusted, sterile saline, or, preferably, as solutions in isotonic, pH adjusted, sterile saline, optionally in combination with a preservative such as a benzylakonium chloride. Alternatively, they may be formulated in an ointment such as petrolatum.

For application topically to the skin, the substances of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The substances of the invention, without proviso, can also be administered together with other neurotrophic agents such as neurotrophic growth factor (NGF), glial derived growth factor, brain derived growth factor, ciliary neurotrophic factor and/or neurotrophin-3. The dosage level of the neurotrophic agent will depend upon the neurotrophic effectiveness of the combination and the route of administration used.

It is to be appreciated that all references herein to treatment include curative, palliative and prophylactic treatment.

Thus the invention further provides:

(i) a pharmaceutical composition comprising a compound of the formula (I) or a pharmaceutically acceptable salt or solvate thereof, together with a pharmaceutically acceptable excipient, diluent or carrier, optionally also containing another neurotrophic agent;

(ii) a compound of the formula (I) or a pharmaceutically acceptable salt, solvate or composition thereof, for use as a medicament;

(iii) the use of a compound of the formula (I), without proviso, or of a pharmaceutically acceptable salt, solvate or composition thereof, for the manufacture of a medicament for the treatment of neuronal degeneration;

(iv) the use of a compound of the formula (I), without proviso, or of a pharmaceutically acceptable salt, solvat or composition thereof, for the manufacture of a medicament for the promotion of neuronal regeneration and outgrowth;

(v) the use of a compound of the formula (I), without proviso, or of a pharmaceutically acceptable salt, solvate or composition thereof, for the manufacture of a medicament for the treatment of a neurological disease or disorder such as a neurodegenerative disease;

(vi) use as in (v) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(vii) use as (vi) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus;;

(viii) a method of treatment of a human to treat neuronal degeneration which comprises treating said human with an effective amount of a compound of the formula (I), without proviso, or with a pharmaceutically acceptable salt, solvate or composition thereof;

(ix) a method of treatment of a human to promote neuronal regeneration and outgrowth which comprises treating said human with an effective amount of a compound of the formula (I), without proviso, or with a pharmaceutically acceptable salt, solvate or composition thereof;

(x) a method of treatment of a human to treat a neurological disease or disorder such as a neurodegenerative disease which comprises treating said human with an effective amount of a compound of the formula (I), without proviso, or with a pharmaceutically acceptable salt, solvate or compositon thereof;

(xi) a method as in (x) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracid outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g., multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases; and (xii) a method as in (xi) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus.

The following Examples illustrate the preparation of the compounds of the formula (I). It is to be appreciated that where the compound of the Example and/or Preparation is a benzimidazole, the valence tautomer is also disclosed. In the following Examples and Preparations, room temperature means 20 to 25° C. Flash chromatography refers to column chromatography on silica gel (Kieselgel 60, 230–400 mesh). Melting points are uncorrected. $^1$H Nuclear magnetic resonance (NMR) spectra were recorded using a Bruker AC300, a Varian Unity Inova-300 or a Varian Unity Inova-400 spectrometer and were in all cases consistent with the proposed structures. Characteristic chemical shifts are given in parts-per-million downfield from tetramethylsilane using conventional abbreviations for designation of major peaks: e.g. s, singlet; d, doublet; t, triplet; q, quartet; m, multiplet; br, broad. Mass spectra were recorded using a Finnigan Mat. TSQ 7000 or a Fisons Instruments Trio 1000 mass spectrometer. MS means low resolution mass spectrum and the calculated and observed ions quoted refer to the isotopic composition of lowest mass. Hexane refers to a mixture of hexanes (hplc grade) b.p. 65–70° C. Ether refers to diethyl ether. Acetic acid refers to glacial acetic acid. Optical rotatons were determined at 25° C. The nomenclature of the compounds mentioned below was generated by an IUPAC nomenclature program.

Example 1

(2S)-1-(1,3-Benzoxazol-2-yl)-N$^2$-(2-piperidinoethyl)-2-piperidinecarboxamide

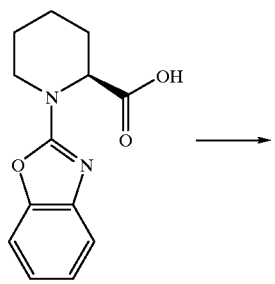

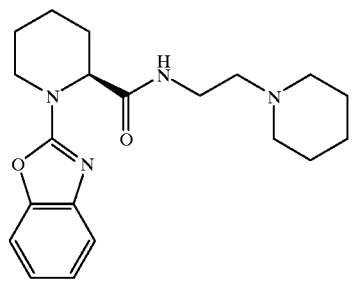

N-methylmorpholine (0.085 ml) was added to a solution of (2S)-1-(1,3-benzoxazol-2-yl)-2-piperidinecarboxylic acid (95.5 mg) [see Preparation 3], hydroxybenzotriazole hydrate (89.0 mg), 2-piperidinoethylamine (50 mg) [see J. Chem. Soc, (1935), 1421–1426] and 1-(3-dimethylaminopropyl)-3-ethylcarbodiimide hydrochloride (140 mg) in dichloromethane (20 ml). The reaction mixture was stirred at room temperature for 18 hours, after which time the mixture was diluted with water and the organic layer was separated, dried over magnesium sulphate and the solvent removed under reduced pressure. The crude product was purified by coloumn chromatography on silica gel eluting with a solvent gradient of 4:1:0, changing to 0:95:5, by volume, hexane: ethyl acetate: 0.88 aqueous ammonia solution solution to afford (2S)-1-(1,3-benzoxazol-2-yl)-N$^2$-(2-piperidinoethyl)-2-piperidinecarboxamide (109 mg) as a white solid.

$^1$H-NMR (CDCl$_3$)δ: 7.40 (1H, d), 7.25 (1H, d), 7.20 (1H, t), 7.00 (1H, t), 6.95 (1H, bs), 4.95 (1H, bs), 4.25 (1H, d), 3.45 (1H, m), 3.30 (2H, m), 2.40 (3H, m), 2.25 (4H, bs), 1.80–1.60 (5H, m), 1.30 (6H, m). MS: 357 (MH$^+$).

Analysis: Found C, 61.65; H, 7.47; N, 13.64; C$_{20}$H$_{28}$N$_4$O$_2$.1.75 H$_2$O. 0.05 CH$_2$Cl$_2$ requires C, 61.36; H, 8.13; N, 14.30%.

Example 2

(2S)-N$^2$-(2-Aminoethyl)-1-(1,3-benzoxazol-2-yl)-2-piperidinecarboxamide

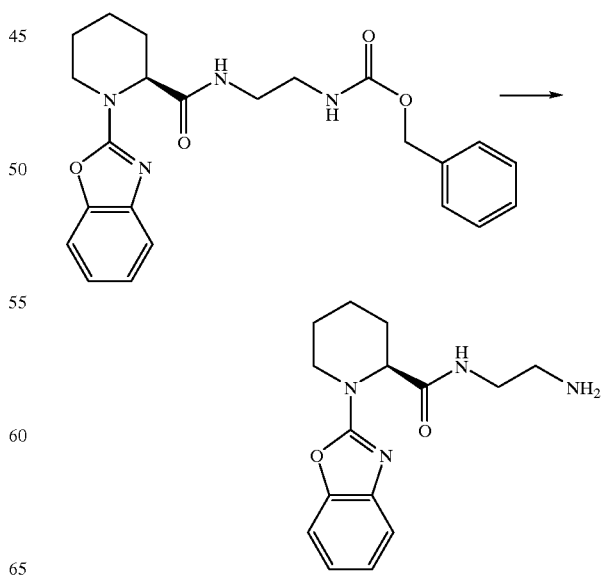

Benzyl N-[2-([(2S)-1-(1,3-benzoxazol-2-yl)-2-piperidinyl]carbonylamino) ethyl]carbamate (480.6 mg) [see Preparation 4] was dissolved in metanol (20 ml) and 10% palladium on charcoal (48 mg) was added. The reaction mixture was then hydrogenated at 4 atmospheres (60 p.s.i.) at room temperature for 3 hours, after which time the mixture was filtered and the solvent removed under reduced pressure. The product was then azeotroped with dichloromethane to afford (2S)-N²-(2-aminoethyl)-1-(1,3-benzoxazol-2-yl)-2-piperidinecarboxamide (296 mg) as a colourless liquid.

$^1$H-NMR (CDCl$_3$)δ:7.40 (1H, d), 7.25 (1H, d), 7.20 (1H, t), 7.05 (1H, t), 6.75 (1H, bs), 4.90 (1H, s), 4.25 (1H, d), 3.40–3.20 (3H, m), 2.80 (2H, t), 2.40 (1H, d), 1.80–1.60 (3H, m), 1.60–1.40 (4H, m). MS: 289 (MH$^+$).

Analysis: Found C, 57.13; H, 6.69; N, 16.27; C$_{15}$H$_{20}$N$_4$O$_2$. 0.5 CH$_2$Cl$_2$ requires C, 57.05; H, 6.28; N, 16.63%.

Example 3

(2S)-1-(1,3-Benzoxazol-2-yl)-N²-2-[(cis)-2,6-dimethyl-1-piperidinyl]ethyl-2-piperidinecarboxamide

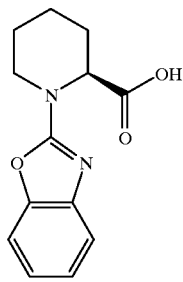

→

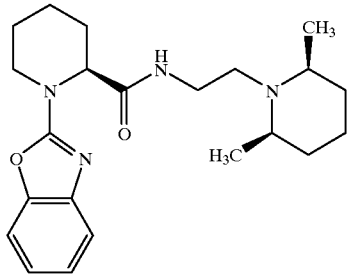

The title compound was prepared by a similar method to Example 1 from (2S)-1-(1,3-benzoxazol-2-yl)-2-piperidinecarboxylic acid [see Preparation 3] and 2-[(cis)-2,6-dimethyl-1-piperidinyl]ethylamine [J. Med. Chem., 27; 5, (1984), 684–691]. The crude product was purified by column chromatography on silica gel eluting with a solvent system of 93:7:1, by volume, dichloromethane:methanol:0.88 aqueous ammonia solution, to afford (2S)-1-(1,3-benzoxazol-2-yl)-N²-2-[(cis)-2,6-dimethyl-1-piperidinyl]ethyl-2-piperidinecarboxamide as a colourless gum.

$^1$H-NMR (CDCl$_3$)δ: 7.40 (1H, d), 7.25 (1H, d), 7.20 (1H, t), 7.05 (1H, t), 6.65 (1H, bs), 5.00 (1H, s), 4.30 (1H, d), 3.40–3.20 (3H, m), 2.80 (2H, m), 2.40 (3H, m), 1.80–1.60 (6H, m), 1.50 (2H, m), 1.40–1.10 (9H, m). MS: 385 (MH$^+$).

Analysis: Found C, 67.63; H, 8.40; N, 14.38; C$_{22}$H$_{32}$N$_4$O$_2$. 0.1 CH$_2$Cl$_2$ requires C, 67.54; H, 8.26; N, 14.26%.

Examples 4 to 7

The compounds of the following tabulated examples (Table 1) of the general formula:

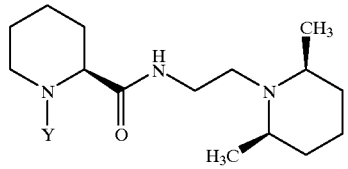

were prepared by a similar method to that described above for Example 1 from 2-[(cis)-2,6-dimethyl-1-(2H)-piperidinyl]ethylamine [J. Med. Chem. 27; 5, (1984), 684–691] and the corresponding carboxylic acid.

TABLE 1

| Example No | Starting material prep. No. | Y | Analytical Data |
|---|---|---|---|
| 4 | 18 | ![structure: 5-methylbenzoxazol-2-yl] | $^1$H-NMR (CDCl$_3$) δ: 7.15 (2H, m), 6.85 (1H, d), 6.80 (1H, bs), 4.95 (1H, s), 4.25 (1H, d), 3.35 (2H, m), 3.20 (1H, t), 2.80 (2H, m), 2.50–2.40 (3H, m), 2.40 (3H, s), 1.80–1.60 (6H, m), 1.50 (2H, t), 1.40–1.10 (9H, m). Accurate Mass: Observed Mass, 399.2762 (MH$^+$), C$_{23}$H$_{35}$N$_4$O$_2$ requires 399.2760 (MH$^+$). Rotation: [α]$_D$ = −48.0° (c = 0.1 methanol) |

TABLE 1-continued

| Example No | Starting material prep. No. | Y | Analytical Data |
|---|---|---|---|
| 5 | 29 | 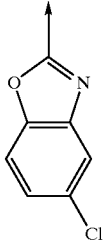 | ¹H-NMR (CDCl₃) δ: 7.30 (1H, d), 7.15 (1H, d), 7.00 (1H, m), 6.80 (1H, bs), 4.95 (1H, s), 4.25 (1H, d), 3.40–3.20 (3H, m), 2.80 (2H, bs), 2.50 (2H, bs), 2.40 (1H, d), 1.80–1.00 (17H, m). Accurate Mass: Found 419.2215 (MH⁺). $C_{22}H_{32}N_4O_2Cl$ requires 419.2214 (MH⁺). |
| 6 | 31 | 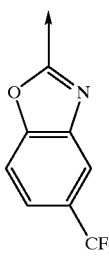 | ¹H-NMR (CDCl₃) δ: 7.60 (1H, s), 7.35 (1H, d), 7.30 (1H, d), 4.95 (1H, s), 4.30 (1H, d), 3.40 (3H, m), 2.80–2.45 (4H, m), 2.40 (1H, d), 1.90–1.10 (17H, m). Accurate Mass: Found 453.2448 (MH⁺). $C_{23}H_{31}N_4O_2F_3$ requires 453.2477 (MH⁺). |
| 7 | 42 | 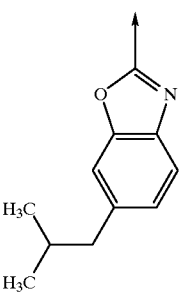 | ¹H-NMR (CDCl₃) δ: 7.25 (1H, m), 7.05 (1H, s), 6.95 (1H, m), 6.65 (1H, bs), 4.95 (1H, s), 4.25 (1H, d), 3.40–3.20 (3H, m), 2.75 (2H, t), 2.55 (2H, d), 2.40 (3H, m), 1.85 (1H, m), 1.80–1.20 (11H, m), 1.15 (6H, m), 0.90 (6H, d). MS: 441 (MH⁺). Rotation: $[\alpha]_D = -95.02°$ (c = 0.1 methanol). |

Example 8

(2S)-1-(1,3-Benzoxazol-2-yl)-N²-2-[(cis)-2,6-dimethyl-1-piperazinyl]ethyl-2-piperidinecarboxamide

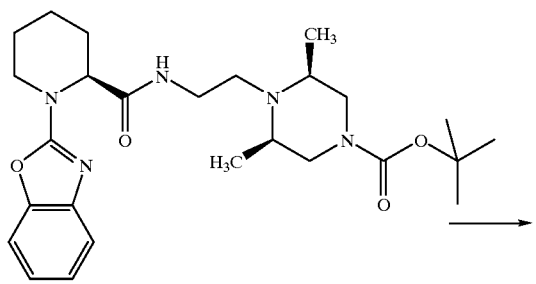

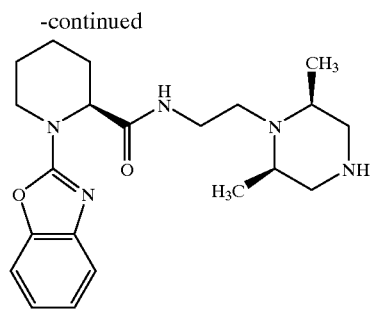

Trifluoroacetic acid (10 ml) was added to a solution of tert-butyl (cis)-4-[2-([(2S)-1-(1,3-benzoxazol-2-yl)-2-piperidinyl]carbonylamino)ethyl]-3,5-dimethyl-1-piperazinecarboxylate (0.95 g) [see Preparation 8] in dichloromethane (10 ml) at 0° C. The reaction mixture was then stirred at room temperature for 1.5 hours, after which time the solvent was removed under reduced pressure and the residue partitioned between saturated potassium carbonate solution and ethyl acetate. The organic layer was separated, dried over magnesium sulphate and the solvent removed under reduced pressure. The product was azeotroped several times with dichloromethane to afford (2S)-1-(1,3- benzoxazol-2-yl)-N²-2-[(cis)-2,6-dimethyl-1-piperazinyl]
ethyl-2-piperidinecarboxamide (0.65 g) as a white foam.

¹H-NMR (CDCl₃)δ: 7.40 (1H, m), 7.25 (1H, m), 7.20 (1H, m), 7.00 (1H, m), 6.60 (1H, bs), 4.95 (1H, s) 4.30 (1H, d), 3.40–3.20 (3H, m), 2.80 (4H, m), 2.50–2.30 (5H, m), 1.80–1.60 (6H, m), 1.00 (6H, m).

Analysis: Found C, 62.08; H, 8.04; N, 16.98; $C_{21}H_{31}N_5O_2$. 0.5 $H_2O$. 0.2 $CH_2Cl_2$ requires C, 61.88; H, 7.94; N, 17.02%. Rotation: $[\alpha]_D$=−78.0° (c=0.1 methanol). MS: 387 (MH⁺).

Example 9

(2S)-N²-2-[(cis)-4-Acetyl-2,6-dimethyl-1-piperazinyl]ethyl-1-(1,3-benzoxazol-2-yl)-2-piperidinecarboxamide

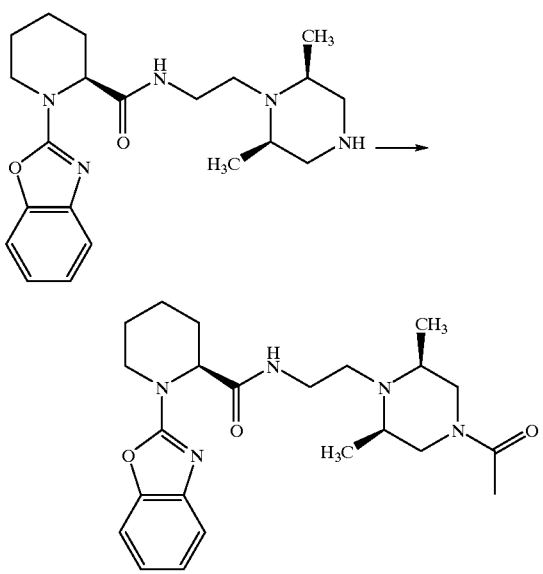

Acetyl chloride (0.018 ml) was added to a solution of (2S)-1-(1,3-benzoxazol-2-yl)-N²-2-[(cis)-2,6-dimethyl-1-piperazinyl]ethyl-2-piperidinecarboxamide (0.1 g) [See Example 8] and potassium carbonate (36 mg) in acetonitrile (2 ml). The reaction mixture was stirred at room temperature for 2 hours, after which time the solvent was removed under reduced pressure and the residue partitioned between ethyl acetate and water. The organic layer was separated, dried over magnesium sulphate and the solvent removed under reduced pressure. The crude product was purified by column chromatography on silica gel eluting with a solvent gradient of 97:3.5:0.5 changing to 97:3:1, by volume, dichloromethane: methanol: 0.88 aqueous ammonia solution (93:7:1), to afford (2S)-N²-2-[(cis)-4-acetyl-2,6-dimethyl-1-piperazinyl]ethyl-1-(1,3-benzoxazol-2-yl)-2-piperidinecarboxamide (91.6 mg) as a white foam.

¹H-NMR (CDCl₃)δ: 7.40 (1H, d), 7.25 (1H, d), 7.20 (1H, t), 7.00 (1H, t), 6.60 (1H, m), 4.95 (1H, s), 4.30–4.15 (2H, m) 3.40–3.15 (4H, m), 2.75 (3H, m), 2.50 (3H, m), 2.30 (1H, q), 2.00 (3H, s), 1.80–1.60 (5H, m), 1.10 (6H, m).

Analysis: Found C, 62.64; H, 7.79; N, 15.73; $C_{23}H_{33}N_5O_3$. 0.1$H_2O$. 0.4 $CH_2Cl_2$ requires C, 62.43; H, 7.59; N, 15.69%. Rotation: $[\alpha]_D$=−67.0° (c=0.1 methanol). MS: 428 (MH⁺).

Example 10

(2S)-1-(1,3-Benzoxazol-2-yl)-N²-2[(cis)-2,4,6-trimethyl-1-piperazinyl]ethyl-2-piperidinecarboxamide

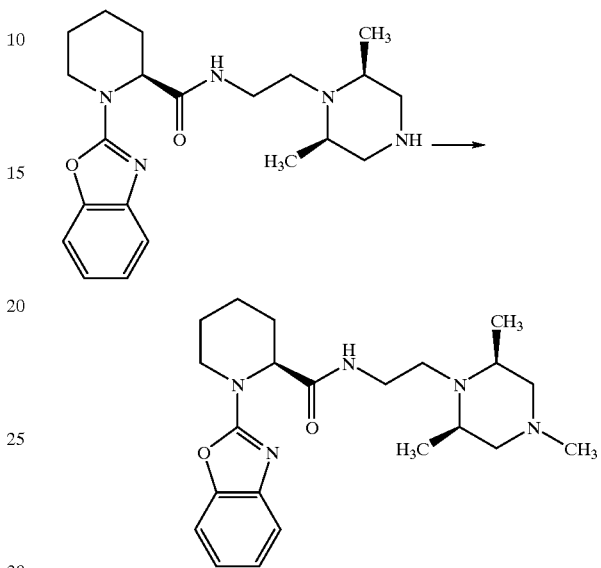

A solution of (2S)-1-(1,3-benzoxazol-2-yl)-N²-2-[(cis)-2,6-dimethyl-1-piperazinyl]ethyl-2-piperidinecarboxamide (108 mg) [see Example 8] and 37% aqueous formaldehyde (0.21 ml) in acetonitrile (3 ml) was added to sodium cyanoborohydride (86.5 mg), followed by glacial acetic acid (0.1 ml). The reaction mixture was stirred at room temperature for 1.5 hours, after which time glacial acetic acid (0.1 ml) was added, and the mixture was stirred for a further 30 minutes. Diethyl ether was added to the mixture and the organic layer was washed several times with 2N aqueous sodium hydroxide solution. The organic layer was separated, dried over magnesium sulphate and the solvent removed under reduced pressure. The crude product was purified by column chromatography on silica gel eluting with a solvent gradient of 97:3.5:0.5 changing to 97:3:1, by volume, dichloromethane: methanol: 0.88 aqueous ammonia solution to afford (2S)-1-(1,3-benzoxazol-2-yl)-N²-2-[(cis)-2,4,6-trimethyl-1-piperazinyl]ethyl-2-piperidinecarboxamide (53.1 mg) as a white solid.

¹ H-NMR (CDCl₃)δ: 7.40 (1H, d), 7.25 (1H, d), 7.20 (1H, t), 7.00 (1H, t), 6.65 (1H, bs), 4.95 (1H, s), 4.35 (1H, d), 3.40–3.20 (3H, m), 2.80 (2H, t), 2.60 (4H, m), 2.40 (1H, d), 2.10 (3H, s), 1.80–1.60 (7H, m), 1.05 (6H, m).

Analysis: Found, C, 65.17; H, 8.33; N, 17.28; $C_{22}H_{33}N_5O_2$. 0.3 $H_2O$ requires C, 65.25; H, 8.36; N, 17.29%. Rotation: $[\alpha]_D$=−73.0° (c=0.1 methanol). MS: 400 (MH ).

Example 11

(cis)-4-[2-([(2S)-1-(1,3-Benzoxazol-2-yl)-2-piperidinyl]carbonylamino)ethyl]-N$^1$-isopropyl-3,5-dimethyl-1-piperazinecarboxamide

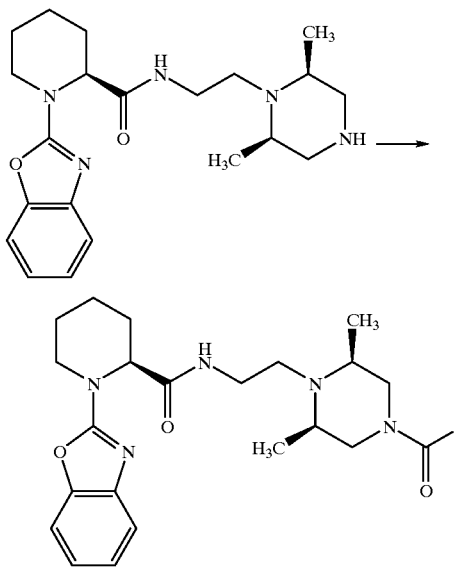

Isopropylisocyanate (0.029 ml) was added to a solution of (2S)-1-(1,3-benzoxazol-2-yl)-N$^2$-2-[(cis)-2,6-dimethyl-1-piperazinyl]ethyl-2-piperidinecarboxamide (105 mg) [see Example 8] and potassium carbonate (37.5 mg) in acetonitrile (3. ml). The reaction mixture was stirred at room temperature for 5 hours, after which time the solvent was removed under reduced pressure and the residue partitioned between ethyl acetate and water. The organic layer was separated, dried over magnesium sulphate and the solvent removed under reduced pressure. The crude product was purified by column chromatography on silica gel eluting with a solvent gradient of 94.6:5.6:0.8 changing to 93:7; 1, by volume, dichloromethane: methanol: 0.88 aqueous ammonia solution to afford (cis)-4-[2-([(2S)-1-(1,3-benzoxazol-2-yl)-2-piperidinyl]carbonylamino)ethyl]-N$^1$-isopropyl-3,5-dimethyl-1-piperazinecarboxamide (72.8 mg) as a white solid.

$^1$H-NMR (CDCl$_3$)δ: 7.35 (1H, d), 7.25 (1H, d), 7.15 (1H, t), 7.00 (1H, t), 4.90 (1H, s), 4.25 (1H, d), 3.90 (1H, m), 3.70–3.10 (6H, m), 2.90–2.30 (6H, m), 1.80–1.50 (5H, m), 1.10 (12H, m).

Analysis: Found C, 59.28; H, 8.26; N, 15.99; C$_{25}$H$_{38}$N$_6$O$_3$. 0.75 H$_2$O. 0.35 CH$_2$Cl$_2$ requires C, 59.25; H, 7.89; N, 16.35%. Rotation: [α]$_D$=−38.0° (c=0.1 methanol). MS: 471 (MH$^+$).

Example 12

(2S)-1-(1,3-Benzoxazol-2-yl)-N$^2$-[2-(3,5-dimethylmorpholino)ethyl]-2-piperidinecarboxamide

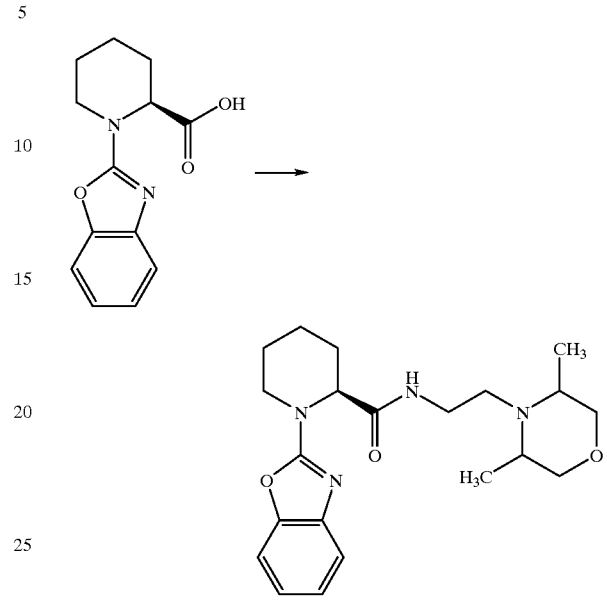

The title compound was prepared by a similar method to Example 1 from (2S)-1-(1,3-benzoxazol-2-yl)-2-piperidinecarboxylic acid [see Preparation 3] and 2-(3,5-dimethylmorpholino)ethylamine [see Preparation 12]. The crude product was purified by column chromatography on silica gel eluting with a solvent gradient of 100:0 changing to 95:5, by volume dichloromethane:methanol to afford (2S)-1-(1,3-benzoxazol-2-yl)-N$^2$-[2-(3,5-dimethylmorpholino)ethyl]-2-piperidinecarboxamide as a solid.

$^1$H-NMR (CDCl$_3$)δ: 7.40 (1H, d), 7.30 (1H, d), 7.20 (1H, t), 7.05 (1H, t), 6.80 (1H, bs), 5.00 (1H, s), 4.30 (1H, d), 3.40–3.00 (6H, m), 2.80 (3H, m), 2.50 (2H, m), 1.80–1.60 (6H, m), 0.95–0.90 (6H, m).

Analysis: Found C, 57.43; H, 6.90; N, 12.17; C$_{21}$H$_{30}$N$_4$O$_3$. 2.25H$_2$O. 0.2 CH$_2$Cl$_2$ requires C, 57.35; H, 7.92; N, 12.62%. Rotation: [α]$_D$=−58.0° (c=0.1 methanol). MS: 387 (MH$^+$).

Example 13

(2S)-N$^2$-3-[(cis)-2,6-Dimethyl-1-piperidinyl]propyl-1-(5-methyl-1,3-benzoxazol-2-yl)-2-piperidinecarboxamide

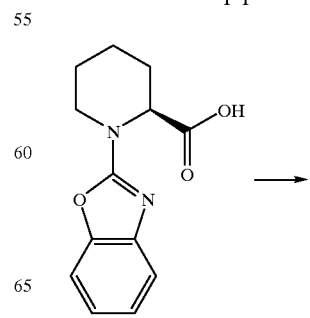

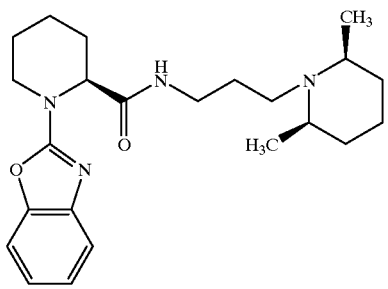

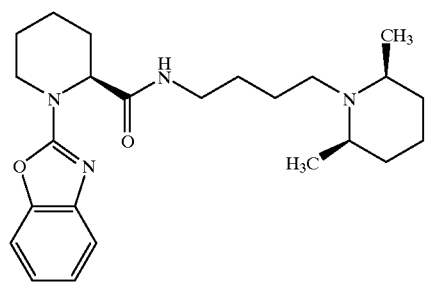

(2S)-1-(1,3-Benzoxazol-2-yl)-2-piperidinecarboxylic acid (270 mg) [see Preparation 3] and 3-[(cis)-2,6-dimethyl-1-piperidinyl]propylamine (180 mg) [J. Am. Chem. Soc. (1971), 71, 3839 and references cited therein] were dissolved in dichloromethane (20 ml). 1-(3-Dimethylaminopropyl)-3-ethylcarbodiimide hydrochloride (290 mg) and a catalytic amount of 4-dimethylaminopyridine were then added to the reaction mixture. The reaction mixture was then stirred at room temperature for 18 hours, after which time the solvent was removed under reduced pressure and the residue partitioned between ethyl acetate and water. The organic layer was separated, dried over sodium sulphate and the solvent removed under reduced pressure. The crude product was purified by column chromatography on silica gel eluting with a solvent system of 20:1, by volume, dichloromethane:methanol to afford (2S)-$N^2$-3-[(cis)-2,6-dimethyl-1-piperidinyl]propyl-1-(5-methyl-1,3-benzoxazol-2-yl)-2-piperidinecarboxamide (37 mg) as a solid.

$^1$H-NMR (CDCl$_3$)δ:7.28 (1H, m), 7.22 (1H, m), 7.10 (1H, m), 7.00 (1H, m), 4.90 (1H, bs), 4.22 (1H, d), 3.40–3.15 (3H, m), 270 (2H, t), 2.40 (1H, d), 2.30 (2H, bs), 1.80–1.30 (10H, m), 1.30–1.05 (4H, m), 0.97 (6H, d).

MS:399 (MH$^+$).

R$_f$:0.35 (5:1, by volume, dichloromethane:methanol).

Example 14

(2S)-1-(1,3-Benzoxazol-2-yl)-$N^2$-4-[(cis)-2,6-dimethyl-1-piperidinyl]butyl-2-piperidinecarboxamide

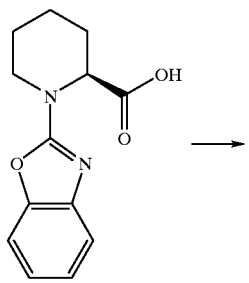

The title compound was prepared and purified by a similar method to Example 13 from (2S)-1-(1,3-benzoxazol-2-yl)-2-piperidinecarboxylic acid [see Preparation 3] and 4-[(cis)-2,6-dimethyl-1-piperidinyl]butylamine [J. Med. Chem. (1984), 27, 684–689] to afford (2S)-1-(1,3-benzoxazol-2-yl)-$N^2$-4-[(cis)-2,6-dimethyl-1(2H)-piperidinyl]butyl-2-piperidinecarboxamide as a solid.

$^1$H-NMR (CDCl$_3$)δ:7.32 (1H, m), 7.25 (1H, m), 7.15 (1H, m), 7.05 (1H, m), 6.60 (1H, bs), 4.20 (1H, d), 3.30 (1H, m), 3.20 (2H, m), 2.75 (2H, m), 2.50–2.30 (3H, m), 1.90 –1.50 (8H, m), 1.50–1.20 (8H, m), 1.00 (6H, t).

MS:413 (MH$^+$).

R$_f$:0.1 (10:1:0.05, by volume, dichloromethane:methanol:0.88 aqueous ammonia solution).

Example 15

(2S)-$N^2$-2-[(cis)-2,6-Dimethyl-1-piperidinyl]ethyl-1-(5-fluoro-1,3-benzoxazol-2-yl)-2-piperidinecarboxamide

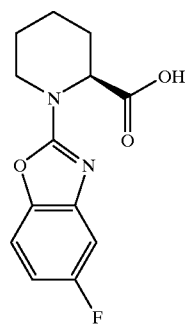

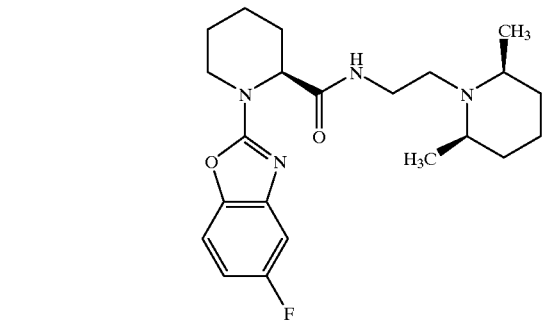

The title compound was prepared and purified by a similar method to Example 13 from (2S)-1-(5-fluoro-1,3-benzoxazol-2-yl)-2-piperidinecarboxylic acid [see Preparation 20] and 2-[(cis)-2,6-dimethyl-1-piperidinyl]ethylamine [J. Med. Chem., 27; 5, (1984), 684–691], to afford (2S)-$N^2$-

2-[(cis)-2,6-dimethyl-1-piperidinyl]ethyl-1-(5-fluoro-1,3-benzoxazol-2-yl)-2-piperidinecarboxamide as a solid.

$^1$H-NMR (CDCl$_3$)δ:7.11 (1H, m), 7.00 (1H, m), 6.80 (1H, bs), 6.70 (1H, m), 4.88 (1H, bs), 4.20 (1H, d), 3.40–3.10 (3H, m), 2.70 (2H, t), 2.50–2.30 (3H, m), 1.80 –1.35 (8H, m), 1.35–1.10 (3H, m), 1.05 (6H, t).

MS:403 (MH$^+$).

R$_f$:0.4 (10:0.5:0.5, by volume, dichloromethane:methanol:0.88 aqueous ammonia solution).

Example 16

(2S)-N$^2$-2-[(cis)-2,6-Dimethyl-1-piperidinyl]ethyl-1-[6-(trifluoromethyl)-1H-1,3-benzimidazol-2-yl]-2-piperidinecarboxamide

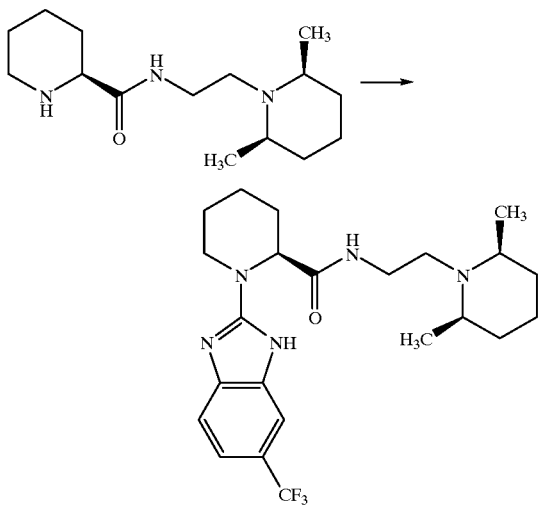

Dimethylacetamide (0.5 ml) was added to a mixture of (2S)-N$^2$-2-[(cis)-2,6-dimethyl-1-piperidinyl]ethyl-2-piperidinecarboxamide (134 mg) [see Preparation 15] and tert-butyl 2-chloro-5-(trifluoromethyl)-1H-1,3-benzimidazole-1-carboxylate (463 mg) [see Preparation 16], the reaction mixture was heated to 80° C. for 12 hours, after which time the mixture was reduced to low volume, xylene (50 ml) was added, and all solvent was removed under reduced pressure. The residue was partitioned between saturated sodium bicarbonate solution and ethyl acetate, the organic layer was separated, dried over magnesium sulphate and the solvent removed under reduced pressure. The crude product was purified by column chromatography on silica gel eluting with a solvent gradient of 100:0, changing to 98:2, by volume, ethyl acetate:diethylamine, in 0.5% increments, to afford (2S)-N$^2$-2-[(cis)-2,6-dimethyl-1-piperidinyl]ethyl-1-[6-(trifluoromethyl)-1H-1,3-benzimidazol-2-yl]-2-piperidinecarboxamide (55 mg) as a white solid.

$^1$-NMR (d4-MeOH)δ:7.50 (1H, s), 7.30 (2H, q), 4.90 (1H, d), 3.90 (1H, d), 3.50–3.40 (2H, m), 2.85 (3H, t), 2.60 (2H, m), 2.30 (1H, d), 1.90–1.20 (11H, m), 1.20 (6H, d).

Analysis:Found C, 60.77; H, 7.16; N, 15.25; C$_{23}$H$_{32}$F$_3$N$_5$O requires C, 61.18; H, 7.14; N, 15.51%.

Rotation:[α]$_D$=−79.0° (c=0.1 methanol)

MS:452 (MH$^+$).

Examples 17–22

The compounds of the following tabulated Examples (Table 2) of the general formula:

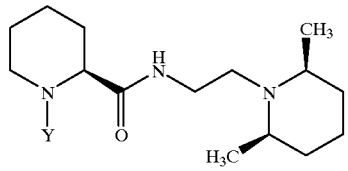

were prepared by a similar method to Example 16 from (2S)-N$^2$-2-[(cis)-2,6-dimethyl-1-piperidinyl]ethyl-2-piperidinecarboxamide [see Preparation 15] and the corresponding benzimidazolyl chloride.

TABLE 2

| Example No. | starting material prep. No. | Y | Analytical data |
|---|---|---|---|
| 17 | 32 | ![benzimidazole] | $^1$H-NMR (d$_4$-MeOH) δ: 7.25 (2H, d), 7.00 (2H, d), 4.85 (1H, s), 3.90 (1H, d), 3.40 (3H, m), 2.80 (2H, m), 2.60 (2H, m), 2.30 (1H, d), 1.80 (3H, m), 1.65 (2H, d), 1.55 (3H, m), 1.40 (1H, t), 1.25 (2H, t), 1.20 (6H, d). Analysis: Found C, 68.20; H, 8.79; N, 17.91; C$_{22}$H$_{33}$N$_5$O. 0.2H$_2$O requires C, 68.25; H, 8.70; N, 18.09%. Rotation: [α]$_D$ = −78.62° (c = 0.1 methanol) |

TABLE 2-continued

| Example No. | starting material prep. No. | Y | Analytical data |
|---|---|---|---|
| 18 | 21 | 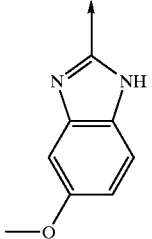 | $^1$H-NMR (d$_4$-MeOH) δ: 7.10 (1H, d), 6.85 (1H, s), 6.60 (1H, d), 4.80 (1H, s), 3.90 (1H, d), 3.80 (3H, s), 3.40–3.20 (3H, m), 2.80 (2H, m), 2.60 (2H, m), 2.25 (1H, d), 1.80–1.25 (11H, m), 1.20 (6H, d). Analysis: Found C, 65.69; H, 8.87; N, 16.04; C$_{23}$H$_{35}$N$_5$O$_2$. 0.5H$_2$O. 0.1hexane requires C, 65.86; H, 8.57; N, 16.27%. Rotation: [α]$_D$ = −78.40° (c = 0.1 methanol) |
| 19 | 22 | 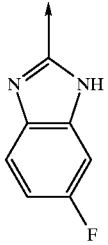 | $^1$H-NMR (d$_4$-MeOH) δ: 7.25 (1H, m), 7.05 (1H, d), 6.90 (1H, t), 4.80 (1H, m), 3.85 (1H, d), 3.60–3.40 (7H, m), 2.35 (1H, d), 2.00–1.45 (11H, m), 1.40 (6H, d). Accurate mass: Found 401.2588 (M$^+$) C$_{22}$H$_{32}$N$_5$OF requires 401.2591 |
| 20 | 23 | 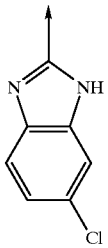 | $^1$H-NMR (d$_4$-MeOH) δ: 7.25 (1H, s), 7.15 (1H, d), 6.95 (1H, d), 4.80 (1H, s), 3.90 (1H, d), 3.40 (3H, m), 2.80 (2H, m), 2.60 (2H, m), 2.30 (1H, d), 1.80–1.25 (11H, m), 1.20 (6H, d). Accurate mass: Found 418.2382 (MH$^+$) C$_{22}$H$_{33}$N$_5$OCl requires 418.2373 (MH$^+$). |
| 21 | 26 | 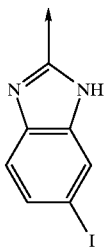 | $^1$H-NMR (d$_4$-MeOH) δ: 7.55 (1H, s), 7.30 (1H, d), 7.05 (1H, d), 4.80 (1H, s), 3.90 (1H, d), 3.40–3.20 (3H, m), 2.80 (2H, m), 2.55 (2H, m), 2.30 (1H, d), 1.80–1.25 (11H, m), 1.20 (6H, d). Analysis: Found C, 49.56; H, 6.18; N, 12.97; C$_{22}$H$_{32}$N$_5$OI. 1.2H$_2$O requires C, 49.76; H, 6.53; N, 13.19%. Rotation: [α]$_D$ = −54.27° (c = 0.1 methanol) |
| 22 | 27 | 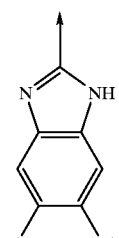 | $^1$H-NMR (d$_4$-MeOH) δ: 7.30 (2H, s), 4.85 (1H, s), 3.85 (1H, d), 3.40–3.20 (3H, m), 3.00–2.60 (4H, m), 2.30 (1H, d), 1.90–1.25 (11H, m), 1.20 (6H, d). Analysis: Found C, 55.39; H, 6.81; N, 14.52; C$_{22}$H$_{31}$N$_5$OCl$_2$. 1.25 H$_2$O requires C, 55.64; H, 7.11; N, 14.75%. Rotation: [α]$_D$ = −84.25° (c = 0.1 methanol) |

Example 23

(2S)-N²-2-[(cis)-2,6-Dimethylcyclohexyl]ethyl-1-(5-methoxy-1,3-benzoxazol-2-yl)-2-piperidinecarboxamide

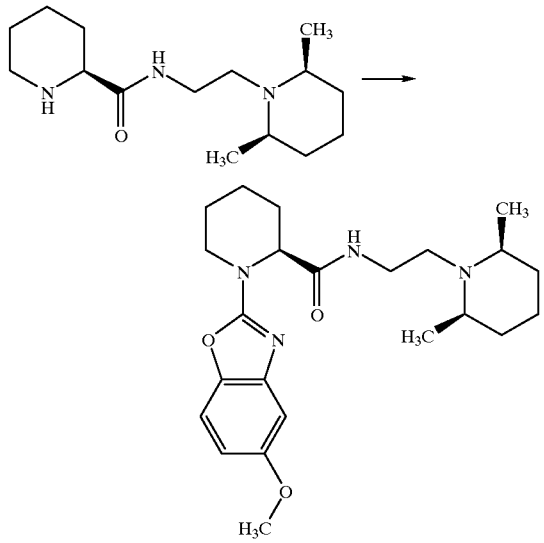

The title compound was prepared by a similar method to Example 16 from (2S)-N²-2-[(cis)-2,6-dimethyl-1-piperidinyl]ethyl-2-piperidinecarboxamide [see Preparation 15] and 2-chloro-5-methoxy-1,3-benzoxazole [see J. Med. Chem (1988), 31, 1719–1728]. The crude product was purified by column chromatography on silica gel eluting with a solvent gradient of 98:2 changing to 90:10, by volume, dichloromethane:methanol, in 1% increments to afford (2S)-N²-2-[(cis)-2,6-dimethylcyclohexyl]ethyl-1-(5-methoxy-1,3-benzoxazol-2-yl)-2-piperidinecarboxamide as an oil.

¹H-NMR (CDCl₃)δ:7.15 (1H, d), 6.90 (1H, s), 6.60 (2H, m), 4.95 (1H, s), 4.25 (1H, d), 3.80 (3H, s), 3.40–3.20 (3H, m), 2.75 (2H, m), 2.40 (3H, bs), 1.80–1.10 (17H, m).

MS:415 (MH⁺).

Rotation:[α]$_D$=−97.42° (c=0.1 methanol)

Example 24

(2S)-N²-2-[(cis)-2,6-Dimethylcyclohexyl]ethyl-1-(5-ethyl-1,3-benzoxazol-2-yl)-2-piperidinecarboxamide

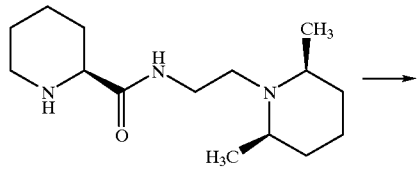

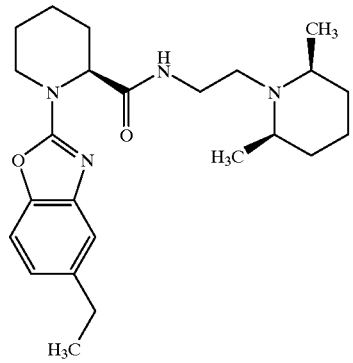

The title compound was prepared by a similar method to Example 16 from (2S)-N²-2-[(cis)-2,6-dimethyl-1-piperidinyl]ethyl-2-piperidinecarboxamide [see Preparation 15] and 2-chloro-5-ethyl-1,3-benzoxazole [see J. Med. Chem (1988), 31, 1719–1728]. The crude product was purified by column chromatography on silica gel eluting with a solvent gradient of 98:2 changing to 90:10, by volume, dichloromethane:methanol, in 1% increments to afford (2S)-N²-2-[(cis)-2,6-dimethylcyclohexyl]ethyl-1-(5-ethyl-1,3-benzoxazol-2-yl)-2-piperidinecarboxamide as an oil.

¹H-NMR (CDCl₃)δ:7.25 (1H, s), 7.20 (1H, d), 6.90 (1H, d), 6.80 (1, bs), 4.95 (1H, s), 4.30 (1H, d), 3.40–3.20 (3H, m), 2.80–2.70 (4H, m), 2.45 (3H, m), 1.90–1.10 (20H, m).

MS:413 (MH⁺).

Rotation:[α]$_D$=−127.83° (c=0.1 methanol).

Example 25

(2S)-N²-2-[(cis)-2,6-dimethyl-1-piperidinyl]ethyl-1-(6-isopropoxy-1,3-benzoxazol-2-yl)-2-piperidinecarboxamide

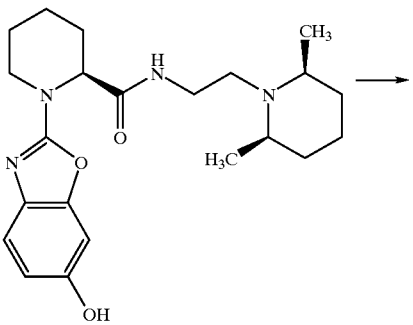

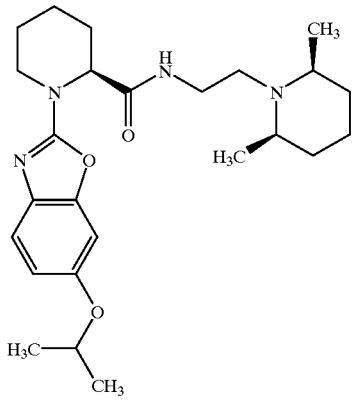

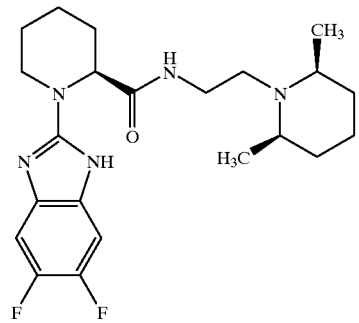

Sodium hydride as a 60% dispersion in oil (6 mg) was added to a solution of (2S)-N-2-[(cis)-2,6-dimethyl-1-piperidinyl]ethyl-1-(6-hydroxy-1,3-benzoxazol-2yl)-2-piperidinecarboxamide (54.5 mg) [see Preparation 39] in dimethylformamide (2 ml) at 0° C. After 5 minutes 2-iodopropane (0.014 ml) were added. The reaction mixture was stirred at room temperature for 4 hours, after which time sodium hydride (3 mg) followed by 2-idodpropane (0.007 ml) was added. The mixture was stirred for a further 18 hours, after which time the solvent was removed and the residue partitioned between water and diethyl ether. The organic layer was separated, dried over magnesium sulphate and the solvent removed under reduced pressure. The crude product was purified by column chromatography on silica gel eluting with a solvent system of 97:3.5:0.5, by volume, dichloromethane/methanol/0.88 aqueous ammonia solution to afford (2S)-N-2-[(cis)-2,6-dimethyl-1-piperidinyl]ethyl-1-(6-isopropoxy-1,3-benzoxazol-2-yl)-2-piperidinecarboxamide (24 mg) as a brown solid.

$^1$H-NMR (CDCl$_3$)δ:7.25 (1H, d), 6.90 (1H, s), 6.80 (1H, d), 6.65 (1H, bs), 4.90 (1H, s), 4.45 (1H, m), 4.25 (1H, d), 3.40–3.15 (3H, m), 2.75 (2H, m), 2.40 (3H, m), 1.80–1.00 (23H, m).

MS:444 (MH$^+$).

Analysis:Found C, 75.43; H, 8.50; N, 12.07; C$_{25}$H$_{38}$N$_4$O$_3$. 0.785 H$_2$O required C. 75.83; H, 8.73; N, 12.28%.

Rotation:[α]$_D$=−76.00° (c=0.1 methanol).

Example 26

(2S)-N$^2$-[(cis)-2,6-Dimethyl-1-piperidinyl]ethyl-1-[5,6-difluoro-1H-1,3-benzimidazol-2-yl]-2-piperidinecarboxamide

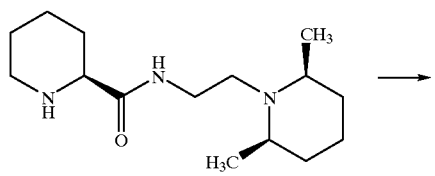 →

Dimethylacetamide (1 ml) was added to a mixture of (2S)-N$^2$-2-[(cis)-2,6-dimethyl-1-piperidinyl]ethyl-2-piperidinecarboxamide (267 mg) [see Preparation 15] and tert-butyl 2-chloro-5,6-difluoro-1H-1,3-benzimidazole-1-carboxylate (350 mg) [see Preparation 43]. The reaction mixture was heated to 60° C. for 4 hours, after which time the mixture was reduced to low volume, xylene (50 ml) was added, and all solvent was removed under reduced pressure. The residue was dissolved in dichloromethane (10 ml) and treated with trifluoroacetic acid (5 ml). After 2 hours stirring at room temperature, the mixture was reduced to low volume. The residue was dissolved in dichloromethane, washed with saturated sodium bicarbonate solution, dried over magnesium sulphate and evaporated to dryness. The crude product was purified by column chromatography on silica gel eluting with a solvent gradient of 100:0, changing 95:4.5:0.5 dichlomethane:methanol:0.880 aqueous ammonia solution to afford (2S)-N$^2$-2-[(cis)-2,6-dimethyl-1-piperidinyl]ethyl-1-[5,6-difluoro-1H-1,3-benzimidazol-2-yl]-2-piperidinecarboxamide (50 mg) as a white solid.

$^1$H-NMR d4-MeOH)δ:7.05 (2H, m), 4.90 (1H, d), 3.90 (1H, d), 3.50–3.40 (3H, m), 2.85 (2H, t), 2.60 (2H, m), 2.30 (1H, d), 1.90–1.20 (11H, m), 1.20 (6H, d).

Analysis:Found C, 60.47; H, 7.33; N, 15.83; C$_{22}$H$_{31}$F$_2$N$_5$O. 0.6 H$_2$O. 0.4 methanol requires C, 60.71; H, 7.69; N, 15.80%.

Rotation:[α]$_D$=−71.7° (c=0.096 methanol)

MS:420 (MH$^+$).

Examples 27–29

The compounds of the following tabulated Examples (Table 3) of the general formula:

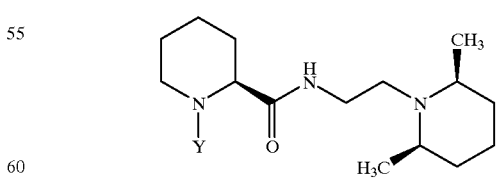

were prepared by a similar method to Example 26, at the temperature and for the time specified from (2S)-N$^2$-2-[(cis)-2,6-dimethyl-1-piperidinyl]ethyl-2-piperidinecarboxamide [see Preparation 15] and the corresponding benzimidazolyl chloride.

TABLE 3

| Example No. | starting material prep. No. | Y | Temp. (°C.) | time (hrs) | Analytical data |
|---|---|---|---|---|---|
| 27 | 44 | ![structure: 4-methyl benzimidazole] | 100 | 18 | $^1$H-NMR (d$_4$-MeOH) δ: 7.08 (1H, d), 6.95 (1H, m), 6.79 (1H, d), 4.85 (1H, s), 3.95 (1H, d), 3.40–3.32 (3H, m), 2.82 (2H, m), 2.62 (2H, m), 2.41 (3H, s), 2.28 (1H, d), 1.90–1.20 (11H, m), 1.20 (6H, d). Analysis: Found C, 66.77; H, 8.84; N, 16.72; C$_{23}$H$_{35}$N$_5$O. H2O requires C, 66.47; H, 8.97; N, 16.85%. Rotation: [α]$_D$ = −63.1° (c = 0.1 methanol) MS: 398 (MH$^+$). |
| 28 | 45 | ![structure: 5-methyl benzimidazole] | 100 | 5 | $^1$H-NMR (d$_4$-MeOH) δ: 7.17 (1H, d), 7.08 (1H, s), 6.85 (1H, d), 4.85 (1H, s), 3.92 (1H, d), 3.40 (3H, m), 2.84 (2H, m), 2.58 (2H, m), 2.42 (3H, s), 2.30 (1H, d), 1.90–1.20 (11H, m), 1.20 (6H, d). Analysis: Found C, 68.12; H, 8.76; N, 17.28; C$_{23}$H$_{35}$N$_5$O. 0.5 H2O requires C, 67.95; H, 8.93; N, 17.23%. Rotation: [α]$_D$ = −85.52° (c = 0.12 methanol) MS: 398 (MH$^+$). |
| 29 | 48 | ![structure: 4-fluoro benzimidazole] | 65 | 16 | $^1$H-NMR (d$_4$-MeOH) δ: 7.05 (1H, m), 6.95 (1H, m), 6.77 (1H, m), 4.85 (1H, s), 3.90 (1H, d), 3.40–3.35 (3H, m), 2.82 (2H, m), 2.60 (2H, m), 2.30 (1H, d), 1.90–1.20 (11H, m), 1.20 (6H, d). Analysis: Found C, 64.04; H, 7.99; N, 16.16; C$_{22}$H$_{32}$FN$_5$O. 0.7 Methanol requires C, 64.31; H, 8.27; N, 16.52%. Rotation: [α]$_D$ = −61.26° (c = 0.096 methanol) MS: 402 (MH$^+$). |

Example 30

(2S)-N$^2$-2-[(cis)-2,6-Dimethyl-1-piperidinyl]ethyl-1-[7-methoxy)carbonyl-1,3-benzoxazol-2-yl]-2-piperidinecarboxamide

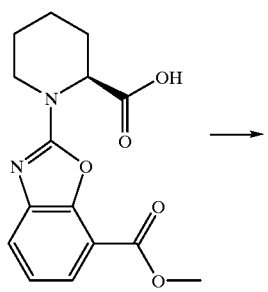

→

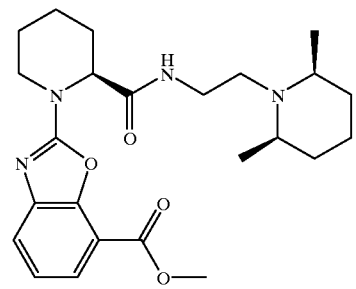

The title compound was prepared by a similar method to Example 1 from (2S)-1-[7-(methoxy)carbonyl-1,3-benzoxazol-2-yl]-2-piperidinecarboxylic acid [see Preparation 51] and 2-[(cis)-2,6-dimethyl-1-piperidinyl]ethylamine [J. Med. Chem., 27(5), (1984), 684–691]. The crude product was purified by column chromatography on silica gel, eluting with a solvent gradient of 100:0:0 changing to 99:1:0 then 80:20:10, by volume, dichloromethane:methanol:0.88 aqueous ammonia solution to afford (2S)-N-2-[(cis)-2,6- dimethyl-1-piperidinyl]ethyl-1-[7-(methoxy)carbonyl-1,3-benzoxazol-2-yl]-2-piperidinecarboxamide as a white solid.

¹H NMR CDCl₃)δ:7.62 (1H, d), 7.50 (1H, d), 7.20 (1H, t), 6.60 (1H, s), 4.95 (1H, s), 4.35 (1H, d), 3.95 (3H, t), 3.30 (3H, m), 2.72 (2H, m), 2.40 (3H, m), 1.79 (4H, m), 1.42 (3H, m), 1.30–1.05 (10H, m)

MS:443.3 (MH⁺)

Analysis:Found C, 63.40; H, 7.59; N, 12.22; C₂₄H₃₄N₄O₄.0.6 H₂O requires C, 63.58; H, 7.83; N, 12.36%.

Rotation: [α]$_D$–90.8° (c=0.124 methanol).

Example 31

(2S)-N²-2-[(cis)-2,6-Dimethyl-1-piperidinyl]ethyl-1-[5,6-dimethyl-1,3-benzoxazol-2-yl]-2-piperidinecarboxamide

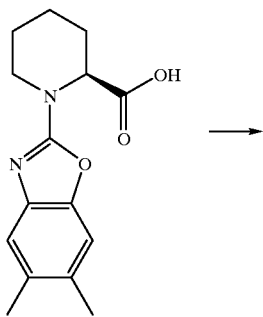

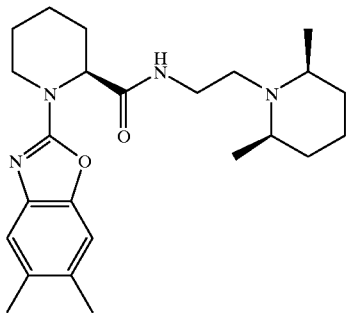

The title compound was prepared by a similar method to Example 1 from (2S)-1-[5,6-dimethyl-1,3-benzoxazol-2-yl]-2-piperidinecarboxylic acid [see Preparation 53] and 2-[(cis)-2,6-dimethyl-1-piperidinyl]ethylamine [J.Med.Chem., 27(5), (1984), 684–691]. The crude product was purified by column chromatography on silica gel, eluting with a solvent gradient of 93:7:1, by volume, dichloromethane:methanol:0.88 aqueous ammonia solution to afford (2S)-N-2-[(cis)-2,6-dimethyl-1-piperidinyl]ethyl-1-[1-(5,6-dimethyl-1,3-benzoxazol-2-yl]-2-piperidinecarboxamide as a white solid.

¹H NMR (CDCl₃)δ:7.15 (1H, s), 7.05 (1H, s), 6.65 (1H, bs), 4.90 (1H, s), 4.20 (1H, d), 3.35 (1H, m), 3.30 (1H, m), 3.20 (1H, t), 2.70 (2H, t), 2.40 (3H, m), 2.30 (6H, s), 1.85–1.55 (6H, m), 1.45 (1H, m), 130–1.05 (10H, m)

MS:413.3 (MH⁺)

Analysis:Found C, 68.87; H, 8.79; N, 13.35; C₂₄H₃₆N₄O₂. 0.25H₂O requires C, 69.12; H, 8.82; N, 13.43%

Rotation: [α]$_D$–90.42° (c=0.1 methanol)

Examples 32–44 are also designated as certain of the Preparations which appear below.

Preparation 1

(2S)-2-(Methoxycarbonyl)piperidinium chloride

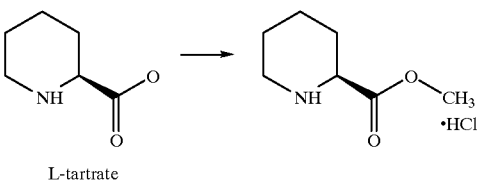

L-tartrate

[(2S)-Piperidinecarboxylic acid L-tartrate (20.0 g) [se International Patent Application publication number WO-A-96/11185] was added dropwise to a solution of thionyl chloride (54 ml) in methanol (270 ml) at 0° C. The reaction mixture was then stirred for 18 hours at room temperature, after which time the solvent was removed under reduced pressure and the residue was azeotroped with toluene (3×100 ml). The crude product was purified by recrystallisation from methanol (15 ml) with addition of diethyl ether to turbidity, affording (2S)-2-(methoxycarbonyl) piperidinium chloride (11.06 g) as white crystals.

¹H-NMR (D₂O)δ:3.95 (1H, d), 3.70 (3H, m), 3.40 (1H, d), 3.00 (1H, t), 2.20 (1H, d), 1.80 (2H, m), 1.70–1.40 (3H, m).

Rotation:[α]$_D$=–8.40° (c=0.1 methanol).

MS:144 (MH⁺).

Preparation 2/Example 32

Methyl (2S)-1-(1,3-benzoxazol-2-yl)-2-piperidinecarboxylate

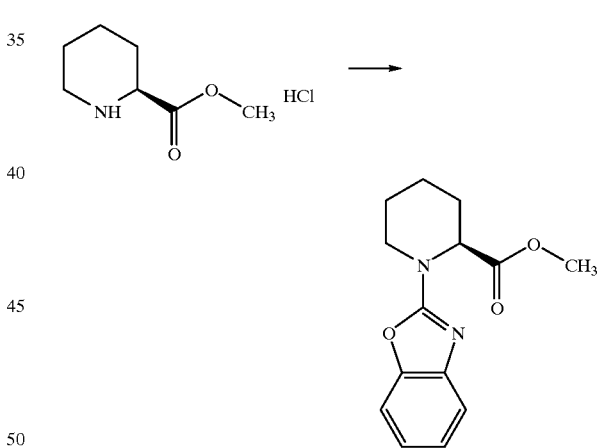

N-Ethyldiisopropylamine (6.52 ml) was added to a solution of (2S)-2-(methoxycarbonyl)piperidinium chloride (3.057 g) [see Preparation 1] and 2-chlorobenzoxazole (2.13 ml) in acetonitrile (50 ml). The reaction mixture was stirred at room temperature for 18 hours and then at 50° C. for a further 2 hours. The solvent was removed under reduced pressure and the residue partitioned between ethyl acetate and water, the organic layer was separated, dried over magnesium sulphate and the solvent removed under reduced pressure. The crude product was purified by column chromatography on silica gel eluting with a solvent gradient of 80:10:0, changing to 0:100:0, followed by 0:95:5, by volume, hexane:ethyl acetate:methanol, to afford methyl (2S)-1-(1,3-benzoxazol-2-yl)-2-piperidinecarboxylate (3.18 g) as a solid.

$^1$H-NMR (CDCl$_3$)δ:7.35 (1H, d), 7.25 (1H, m), 7.00 (1H, m), 5.00 (1H, d), 4.20 (1H, m), 3.70 (3H, s), 3.35 (1H, t), 2.30 (1H, d), 1.80 (3H, m), 1.60 (1H, m), 1.35 (1H, m).

MS:261 (MH$^+$).

Preparation 3

(2S)-1-(1,3-Benzoxazol-2-yl)-2-piperidinecarboxylic acid

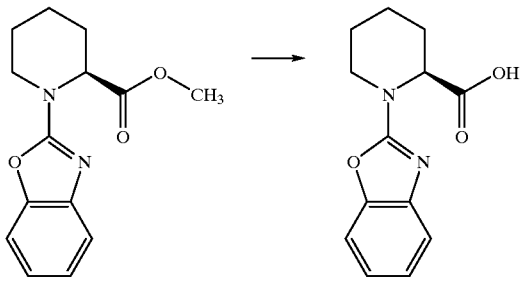

Aqueous lithium hydroxide solution (1N, 51 ml) was added to a solution of methyl (2S)-1-(1,3-benzoxazol-2-yl)-2-piperidinecarboxylate (8.987 g) [see Preparation 2] in methanol (306 ml) at 0° C. The reaction mixture was stirred at room temperature for 18 hours, after which time the solvent was removed under reduced pressure and the residue partitioned between ethyl acetate and water. The aqueous layer was separated and acidified to pH 2 with 2N aqueous hydrochloric acid, the product was extracted with ethyl acetate, dried over magnesium sulphate and the solvent removed under reduced pressure to afford (2S)-1-(1,3-benzoxazol-2-yl)-2-piperidinecarboxylic acid (8.17 g) as a white solid.

$^1$H-NMR (CDCl$_3$)δ:7.40 (1H, d), 7.25 (1H, m), 7.15 (1H, t), 7.00 (1H, t), 5.80 (1H, bs), 4.95 (1H, bs), 4.15 (1H, d), 3.40 (1H, t), 2.40 (1H, d), 1.80 (3H, m), 1.60–1.40 (2H, m).

Rotation:[α]$_D$=−116.2° (c=0.1 methanol).

MS:247 (MH$^+$).

Preparation 4

Benzyl N-[2-([(2S)-1-(1,3-benzoxazol-2-yl)-2-piperidinyl]carbonylamino)ethyl]carbamate

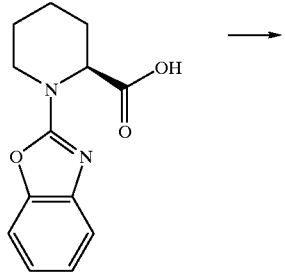

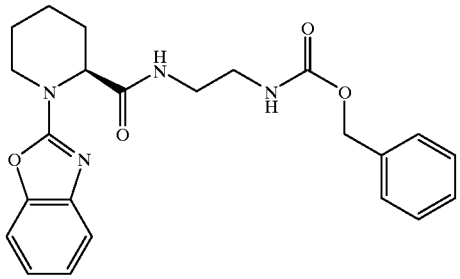

N-methylmorpholine (0.47 ml) was added to a solution of (2S)-1-(1,3-benzoxazol-2-yl)-2-piperidinecarboxylic acid (352.6 mg) [see Preparation 3], hydroxybenzotriazole hydrate (338.4 mg), N-benzyloxycarbonyl-1,2-diaminoethane hydrochloride (499.5 mg) and 1-(3-dimethylaminopropyl)-3-ethylcarbodiimide hydrochloride (552.7 mg) in dichloromethane (15 ml). The reaction mixture was stirred at room temperature for 18 hours, after which time the mixture was diluted with water and the organic layer was separated, dried over magnesium sulphate and the solvent removed under reduced pressure. The crude product was purified by column chromatography on silica gel eluting with a solvent gradient of 1:1, changing to 1:9, by volume, hexane:ethyl acetate to afford benzyl N-[2-([(2S)-1-(1,3-benzoxazol-2-yl)-2-piperidinyl] carbonylamino)ethyl]carbamate (550 mg) as an oil.

$^1$H-NMR (CDCl$_3$)δ:7.40–7.20 (6H, m), 7.10 (1H, t) 7.00 (2H, m), 5.20 (1H, bs), 5.00–4.80 (3H, m), 4.20 (1H, d), 3.45 (1H, m), 3.40–3.10 (5H, m), 2.30 (1H, d), 1.80–1.50 (5H, m).

MS:423 (MH$^+$).

Preparation 5 tert-Butyl (cis)-3,5-dimethyl-1-piperazinecarboxylate

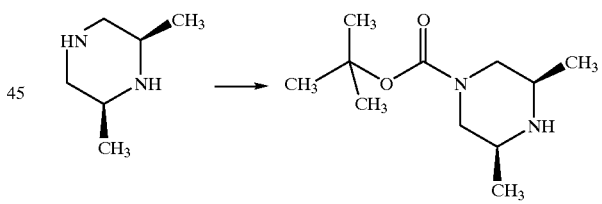

(cis)-3,5-Dimethylpiperazine (5.01 g) was dissolved in dioxan (9 ml) and water (4 ml), di-tert butyldicarbonate (9.59 g) was added and the reaction mixture was stirred at room temperature for 18 hours. The solvent was then removed under reduced pressure and the remaining aqueous solution was basified to pH 9.0 with 2N aqueous sodium hydroxide solution. The product was then extracted twice with ethyl acetate, the combined organic layers were dried over magnesium sulphate and the solvent removed under reduced pressure. The crude product was purified by column chromatography on silica gel eluting with a solvent system of 93:7:1, by volume, dichloromethane:methanol:0.88 aqueous ammonia solution to afford tert-butyl (cis)-3,5-dimethyl-1-piperazinecarboxylate (6.40 g) as a yellow liquid.

$^1$H-NMR (CDCl$_3$)δ:3.90 (2H, bs), 2.80 (2H, m), 2.30 (2H, m), 1.45 (9H, s), 1.40 (1H, bs), 1.05 (6H, d).

MS:215 (MH⁺).

Preparation 6 tert-Butyl (cis)-4-[2-(1,3-dioxo-1,3-dihydro-2H-isoindol-2-yl)ethyl]-3,5-dimethyl-1-piperazinecarboxylate

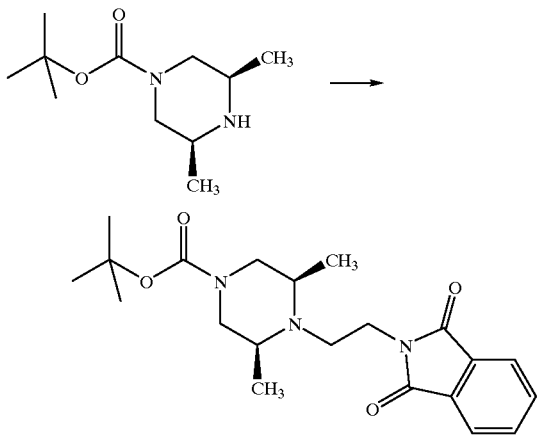

Potassium carbonate (1.79 g) was added to a solution of tert-butyl (cis)-3,5-dimethyl-1-piperazinecarboxylate (2.57 g) [see Preparation 5] in acetronitrile (10 ml). The reaction mixture was stirred at room temperature for 5 minutes, after which time N(2-bromoethyl) phthalimide (3.36 g) was added and the mixture was stirred for a further 4 hours. Sodium iodide (0.1 g) was added and the reaction mixture was heated to reflux for 18 hours. The mixture was then cooled and the solvent removed under reduced pressure. The residue was partitioned between ethyl acetate and water, the organic layer was separated, dried over magnesium sulphate and the solvent removed under reduced pressure. The crude product was purified by column chromatography on silica gel eluting with a solvent gradient of 4:1:0, changing to 0:95:5, by volume, hexane:ethyl acetate:0.88 aqueous ammonia solution. to afford tert-butyl (cis)-4-[2-(1,3-dioxo-1,3-dihydro-2H-isoindol-2-yl)ethyl]-3,5-dimethyl-1-piperazinecarboxylate (0.94 g) as an oil.

¹H-NMR (CDCl₃)δ: 7.85 (2H, m), 7.75 (2H, m), 3.90 (2H, m), 3.75 (2H, t), 2.95 (2H, t), 2.70–2.50 (4H, m), 1.45 (9H, s), 1.20 (6H, d).

MS: 388 (MH⁺).

Preparation 7 tert-Butyl (cis)-4-(2-aminoethyl)-3,5-dimethyl-1-piperazinecarboxylate

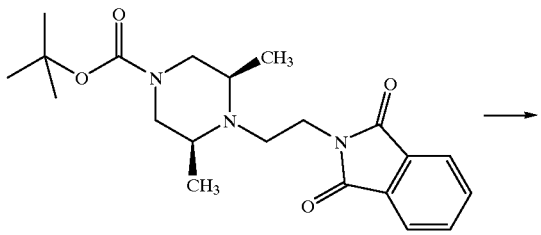

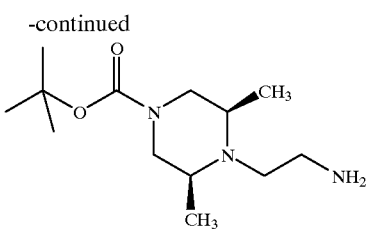

Hydrazine hydrate (0.11 ml) was added to a solution of tert-butyl (cis)-4-[2-(1,3-dioxo-1,3-dihydro-2H-isoindol-2-yl)ethyl]-3,5-dimethyl-1-piperazinecarboxylate (0.736 g) [see Preparation 6] in methanol (1.1 ml). The reaction mixture was then stirred at 50° C. for 18 hours, after which time the solvent was removed under reduced pressure and the residue partitioned between ethyl acetate and 10% citric acid. The aqueous layer was separated, bastified with potassium carbonate, and the product extracted with tetrahydrofuran:ethyl acetate, 1:1, several times. The combined organic layers were dried over magnesium sulphate and the solvent removed under reduced pressure to afford tert-butyl (cis)-4-(2-aminoethyl)-3,5-dimethyl-1-piperazinecarboxylate (0.33 g) as a oil.

¹H-NMR (CDCl₃)δ: 3.80 (2H, bs), 2.80 (4H, m), 2.60 (4H, m), 1.85 (2H, m), 1.45 (9H, s), 1.10 (6H, d).

MS: 258 (MH⁻).

Preparation 8/Example 33 tert-Butyl (cis)-4-[2-([(2S)-1-(1,3-benzoxazol-2-yl)-2-piperidinyl]carbonylamino)ethyl]-3,5-dimethyl-1-piperazinecarboxylate

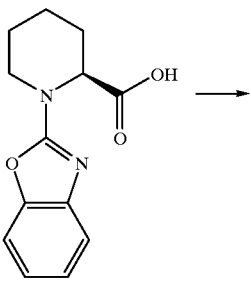

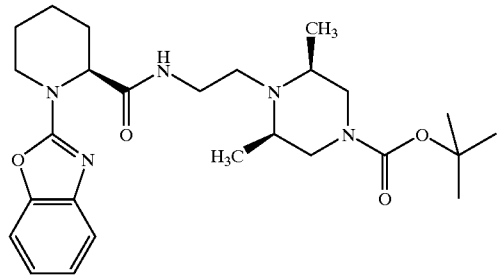

The title compound was prepared by a similar method to Preparation 4 from (2S)-1-(1,3-benzoxazol-2-yl)-2-piperidinecarboxylic acid [see Preparation 3] and tert-butyl (cis)-4-(2-aminoethyl)-3,5-dimethyl-1-piperazinecarboxylate [see Preparation 7]. The crude product was purified by column chromatography on silica gel eluting with a solvent gradient of 4:1:0 changing to 93:7:1, by volume, dichoromethane:methanol:0.88 aqueous ammonia solution in 1% increments to afford tert-butyl (cis)-4-[2-([(2S)-1-(1,3 -benzoxazol-2-yl)-2-piperidinyl]

carbonylamino)ethyl]-3,5-dimethyl-1-piperazinecarboxylate as an oil.

¹H-NMR (CDCl₃)δ: 7.40 (1H, m), 7.25 (1H, m), 7.20 (1H, m), 7.00 (1H, m), 6.60 (1H, bs), 4.95 (1H, s), 4.30 (1H, d), 3.75 (2H, bs), 3.40–3.20 (3H, m), 2.75 (2H, t), 2.45 (5H, m), 1.80–1.60 (5H, m), 1.45 (9H, s), 1.05 (6H, d).

MS: 496 (MH⁺).

Preparation 9

2-[(2-Hydroxy-1-methylethyl)amino]-1-propanol

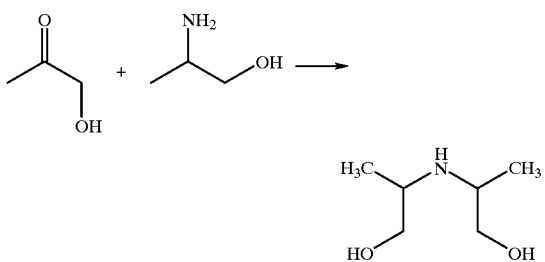

Platinum dioxide (40 mg) was added to a solution of dl-2-amino-1-propanol (6.4 ml) and hydroxyacetone (7.0 g) in methanol (75 ml) over 3 Å molecular sieves. The reaction mixture was hydrogenated at 60 psi. for 18 hours, after which time the catalyst was filtered off and the solvent removed under reduced pressure. The crude product was purified by distillation, b.pt. 94° C.@0.2 mbar to afford 2-[(2-hydroxy-1-methylethyl)amino]-1-propanol (3.66 g) as a yellow oil.

¹H-NMR (CDCl₃)δ: 3.60 (2H, m), 3.30 (2H, m), 2.90 (2H, m), 2.40 (3H, bs), 1.10 (3H, d), 1.05 (3H, d).

Preparation 10

3,5-Dimethyl-1,4-oxazinan-4-ium chloride

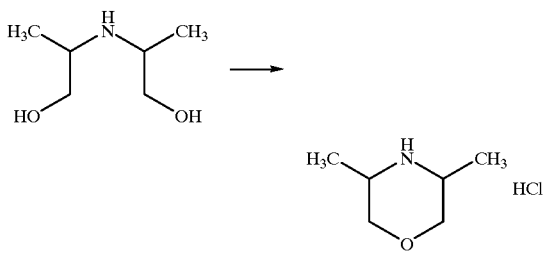

Concentrated sulphuric acid (2.5 ml) was added to 2-[(2-hydroxy-1-methylethyl)amino]-1propanol (3.66 g) [see Preparation 9] at 0° C. with rapid stirring. The reaction mixture was then heated to reflux and stirred for 8 hours. Aqueous potassium hydroxide solution (6.1 g in 31 ml water) was then added to the cooled mixture and a precipitate was formed which was removed by filtration and washed several times with water. The aqueous washings were then combined and acidified with 3M aqueous hydrochloric acid to pH 1, and the water removed under reduced pressure to afford 3,5-dimethyl-1,4-oxazinan-4-ium chloride (3.67 g) as brown crystals.

¹H-NMR (d⁶-DMSO)δ: 9.50 (2H, bs), 3.85 (2H, t), 3.50–3.35 (3H, m), 3.25 (1H, m), 1.25 (3H, d) 1.20 (3H, d).

Preparation 11

2-[2-(3,5-Dimethylmorpholino)ethyl]-1H-isoindole-1,3(2H)-dione

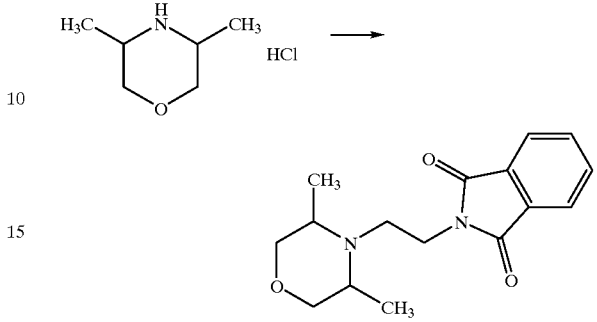

The title compound was prepared by a similar method to Preparation 6 from 3,5-dimethyl-1,4-oxazinan-4-ium chloride [see Preparation 10] and N(2-bromoethyl) phthalimide. The crude produce was purified by column chromatography on silica gel eluting with a solvent system of 8:1, by volume, hexane:ethyl acetate to afford 2-[2-(3,5-dimethylmorpholino)ethyl]-1H-isoindole-1,3(2H)-dione (455 mg) as an oil.

¹H-NMR (CDCl₃)δ: 7.85 (2H, m), 7.70 (2H, m). 3.80–3.60 (4H, m), 3.30 (2H, m), 3.00 (3H, m), 2.60 (1H, m), 1.00 (6H, m).

MS: 289 (MH⁺).

Preparation 12

2-(3,5-Dimethylmorpholino)ethylamine

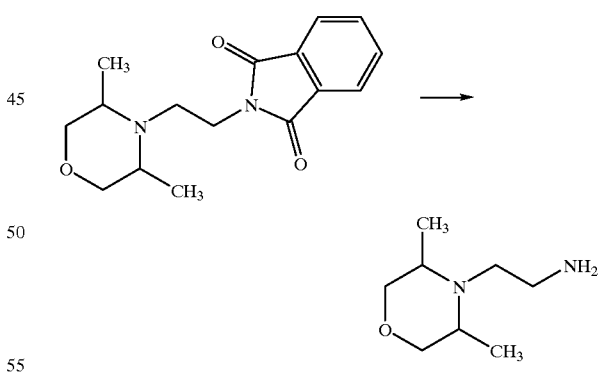

The title compound was prepared by a similar method to Preparation 7 from 2-[2-(3,5-dimethylmorpholino)ethyl]-1H-isoindole-1,3(2H)-dione [see Preparation 11] and hydrazine hydrate, to afford 2-(3,5-dimethylmorpholino)ethylamine as a white solid.

¹H-NMR (CDCl₃)δ: 3.65 (2H, d), 3.40 (2H, m), 2.90–2.50 (8H, m), 1.00 (6H, m).

MS: 159 (MH⁺).

Preparation 13

(2S)-1-(tert-Butoxycarbonyl)-2-piperidinecarboxylic acid

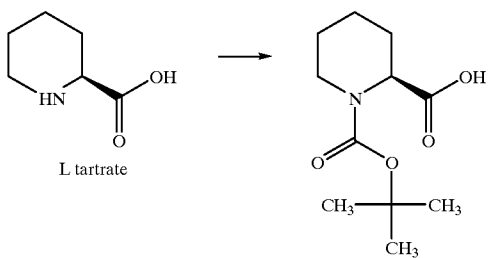

L tartrate

[(2S)-piperidine carboxylic acid L-tartrate (55.0 g) [see WO-A-96/11185] was dissolved in water (200 ml). The resulting solution was cooled to 0° C. and di-t-butyldicarbonate (86 g) in dioxan (203 ml) was added followed by 1N aqueous sodium hydroxide (610 ml) over a period of 20 minutes. The reaction mixture was stirred at 0° C. for 1 hr and then at room temperature for 56 hours. The solvent was then removed under reduced pressure and the resulting solid was dissolved in water (100 ml) and washed with diethyl ether (1000 ml). The aqueous layer was acidified to pH 2.0 with 1M aqueous citric acid (500 ml) and the product was extracted with ethyl acetate (4×500 ml). The combined organic layers were dried over magnesium sulphate and the solvent was removed under reduced pressure to afford (2S)-1-(tert butoxycarbonyl)-2-piperidinecarboxylic acid (19.55 g) as a white solid.

$^1$H-NMR ($d_6$-DMSO)δ: 12.7 (1H, bs), 4.55 (1H, d), 3.80 (1H, s), 2.90–2.60 (1H, m), 2.05 (1H, m), 1.60 (3H, m), 1.30 (10H, d), 1.10 (1H, m).

Preparation 14 tert-Butyl (2S)-2-[(2-[(cis)-2,6-dimethyl-1-piperidinyl]ethylamino)carbonyl]-1-piperidinecarboxylate

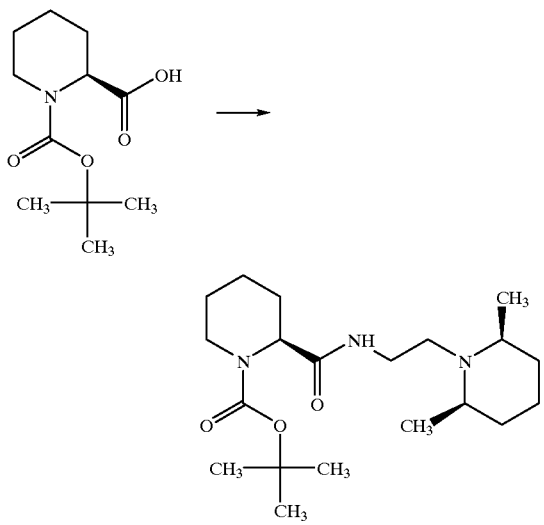

The title compound was prepared by a similar method to Preparation 4 from (2S)-1-(tert butoxycarbonyl)-2-piperidinecarboxylic acid [see Preparation 13] and 2-[(cis)-2,6-dimethyl-1-piperidinyl]ethylamine [J. Med. Chem., 27; 5, (1984), 684–691]. The crude product was purified by column chromatography on silica gel eluting with a solvent gradient of 100:0 changing to 92:8, by volume, dichloromethane:methanol/0.88 aqueous ammonia solution (20/1), in 1% increments to afford tert-butyl (2S)-2-[(2-[(cis)-2,6-dimethyl-1-piperidinyl]ethylamino)carbonyl]-1-piperidinecarboxylate as an oil.

$^1$H-NMR (CDCl$_3$)δ: 6.40 (1H, bs), 4.80 (1H, m), 4.05 (1H, d), 3.30 (2H, m), 2.80 (3H, m), 2.50 (2H, m), 2.30 (1H, m), 1.80–1.30 (20H, m), 1.20 (6H, d).

MS: 368 (MH$^+$).

Preparation 15

(2S)-N$^2$-2-[(cis)-2,6-Dimethyl-1-piperidinyl]ethyl-2-piperidinecarboxamide

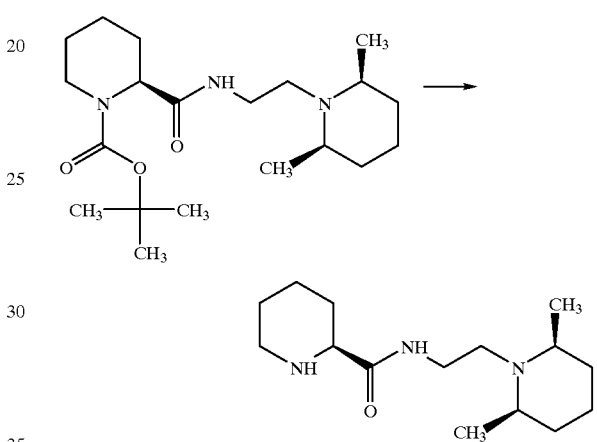

The title compound was prepared by a similar method to Preparation 8 from tert-butyl (2S)-2-[(2-[(cis)-2,6-dimethyl-1-piperidinyl]ethylamino)carbonyl]-1-piperidinecarboxylate [see Preparation 14] and trifluoroacetic acid, to afford (2S)-N$^2$-2-[(cis)-2,6-dimethyl-1-piperidinyl]ethyl-2-piperidinecarboxamide as a gum.

$^1$H-NMR (CDCl$_3$)δ: 3.40 (2H, bs), 3.25 (1H, d), 3.10 (1H, d), 2.90 (3H, bs), 2.70 (2H, t), 2.00 (1H, d), 1.80 (1H, s), 1.75 (1H, s), 1.60 (3H, bs), 1.60–1.50 (6H, m), 1.25 (6H, d).

Rotation: [α]$_D$=−13.1° (c=0.3 methanol).

Preparation 16 tert-Butyl 2-chloro-5-(trifluoromethyl)-1H-1,3-benzimidazole-1-carboxylate

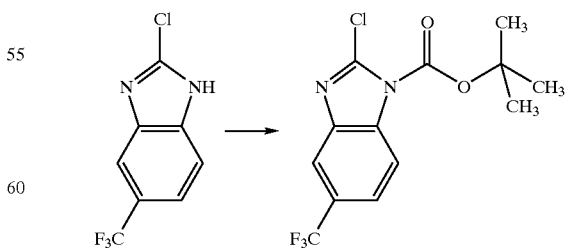

Di-tert-butyldicarbonate (593 mg) was added to a solution of 2-chloro-5-(trifluoromethyl)-1H-1,3-benzimidazole (500 mg) [see JP 02306916 A2 901220] in acetonitrile (5 ml), and dimethylaminopyridine (27 mg) was then added. The reaction mixture was stirred for 10 minutes at room temperature, after which time the solvent was removed under reduced pressure and the residue purified by column chromatography on silica gel eluting with a solvent gradient of 100:0 changing to 85:15, by volume, hexane:ethyl acetate, in 5% increments, to afford tert-butyl 2-chloro-5-(trifluoromethyl)-1H-1,3-benzimidazole-1-carboxylate (678 mg) as a gum, as 1:1 mixture of regioisomers.

$^1$H-NMR (CDCl$_3$)δ: 8.25 (0.5H, s), 8.05 (0.5H, d), 7.95 (0.5H, s), 7.80 (0.5H, d), 7.60 (1H, d), 1.80 (9H, s).

Preparation 17/Example 34

Benzyl (2S)-1-(5-methyl-1,3-benzoaxazol-2-yl)-2-piperidinecarboxylate

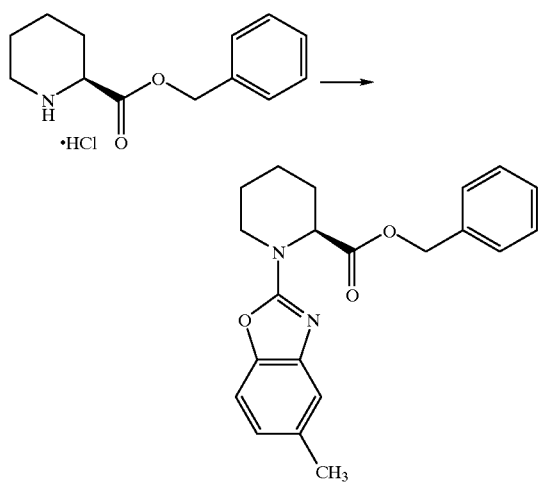

The title compound was prepared by a similar method to Preparation 2 from 2-chloro-5-methyl-1,3-benzoxazole [see J. Med. Chem, 1988, 31, 1719–1728] and (2S)-2-[(benzyloxy)carbonyl]piperidinium chloride [see EP 530167 A1 930303]. The crude product was purified by column chromatography on silica gel eluting with a solvent gradient of 90:10 changing to 70:30, by volume, hexane:ethyl acetate to afford benzyl (2S)-1-(5-methyl-1,3-benzoaxazol-2-yl)-2-piperidinecarboxylate as an oil.

$^1$H-NMR (CDCl$_3$)δ: 7.30 (5H, m), 7.20 (1H, s), 7.15 (1H, d), 6.85 (1H, d), 5.25 (2H, d), 5.10 (1H, d), 4.20 (1H, d), 3.40 (1H, t), 2.40 (3H, s), 2.35 (1H, s), 1.90–1.60 (4H, m), 1.40–1.20 (1H, m).

MS: 351 (MH$^+$).

Preparation 18

(2S)-1-(5-Methyl-1,3-benzoxazol-2-yl)-2-piperidinecarboxylic acid

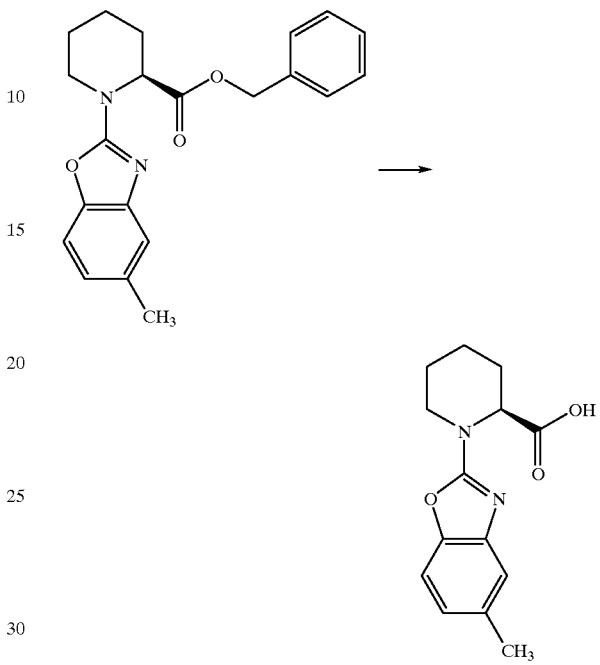

Benzyl (2S)-1-(5-methyl-1,3-benzoxazol-2-yl)-2-piperidinecarboxylate (0.19 g) [see Preparation 17] was dissolved in ethanol (5 ml) and 10% palladium on carbon (0.05 g) was added. The reaction mixture was hydrogenated at 15 psi for 3 hours at room temperature, after which time 10% palladium on carbon (25 mg) was added and the mixture was hydrogenated for a further 1 hr, the catalyst was then filtered off through a plug of arabocel and washed with ethanol. The solvent was removed under reduced pressure to afford (2S)-1-(5-methyl-1,3-benzoaxazol-2-yl)-2-piperidinecarboxylic acid (0.14 g) as a solid.

$^1$H-NMR (CDCl$_3$)δ: 8.05 (1H, bs), 7.20 (1H, s), 7.10 (1H, d), 6.80 (1H, d), 4.90 (1H, d), 4.20 (1H, d), 3.40 (1H, t), 2.40 (1H, m), 2.35 (3H, s), 1.80 (3H, m), 1.60–1.40 (2H, m),

MS: 261 (MH$^+$).

Preparation 19/Example 35

Ethyl (2S)-1-(5-fluoro-1,3-benzoaxazol-2-yl)-2-piperidinecarboxylate

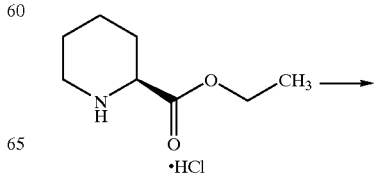

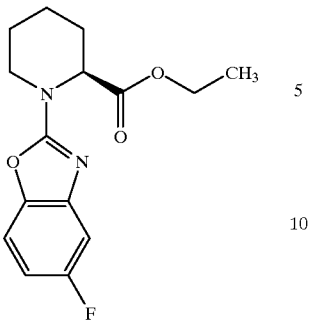

The title compound was prepared by a similar method to Preparation 2 from (2S)-2-(ethoxycarbonyl)piperidinium chloride [see J. Am. Chem. Soc., (1993), 115, 9925–9938] and 2-chloro-5-fluoro-1,3-benzoaxole [see J. Med. Chem. (1988), 31, 1719–1728]. The crude product was purified by column chromatography on silica gel eluting with a solvent system of 3:1, by volume, hexane:ethyl acetate, to afford ethyl (2S)-1-(5-fluoro-1,3-benzoaxazol-2-yl)-2-piperidinecarboxylate as an oil.

$^1$H-NMR (CDCl$_3$)δ: 7.10 (1H, m), 7.00 (1H, m), 6.65 (1H, m), 4.92 (1H, d), 4.15 (3H, m), 3.30 (1H, t), 2.30 (1H, d), 1.80 (3H, m), 1.55 (1H, m), 1.30 (1H, m), 1.20 (3H, t).

Preparation 20

(2S)-1-(5-Fluoro-1,3-benzoxazol-2-yl)-2-piperidinecarboxylic acid

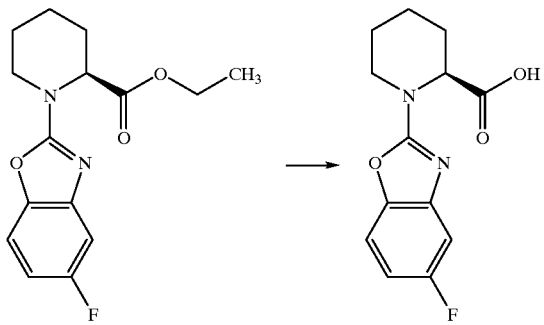

The title compound was prepared by a similar method to Preparation 3 from ethyl (2S)-1-(5-fluoro-1,3-benzoaxazol-2-yl)-2-piperidinylcarboxylate [see Preparation 19] and 1N aqueous lithium hydroxide to afford (2S)-1-(5-fluoro-1,3-benzoaxazol-2-yl)-2-piperidinecarboxylic acid as a solid.

$^1$H-NMR (CDCl$_3$)δ: 11.7 (1H, bs), 7.10 (2H, m), 6.65 (1H, m), 4.90 (1H, d), 4.10 (1H, d), 3.40 (1H, t), 2.40 (1H, d), 1.80 (3H, m), 1.70–1.40 (2H, m).

Preparation 21 tert-Butyl 2-chloro-5-methoxy-1H-1,3-benzimidazole-1-carboxylate

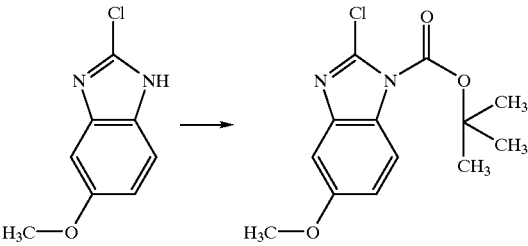

Di-tert-butyldicarbonate (523 mg) was added to a solution of 2-chloro-5-methoxy-1H-1,3-benzimidazole (364 mg) and dimethylaminopyridine (24 mg) in acetonitrile (4 ml). The reaction mixture was stirred at room temperature for 30 minutes, after which time the solvent was removed under reduced pressure. The crude product was purified by column chromatography on silica gel eluting with a solvent gradient of 90:10 changing to 85:15, by volume, hexane:ethyl acetate to afford tert-butyl 2-chloro-5-methoxy-1H-1,3-benzimidazole-1-carboxylate (470 mg) as an off-white solid, as a 1:1 mixture of regioisomers.

$^1$H-NMR (CDCl$_3$)δ: 7.80 (0.5H, d), 7.55 (0.5H, d), 7.50 (0.5H, s), 7.15 (0.5H, s), 7.00 (1H, t), 3.85 (3H, s), 1.70 (9H, s).

Preparation 22 tert-Butyl 2-chloro-6-fluoro-1H-1,3-benzimidazole-1-carboxylate

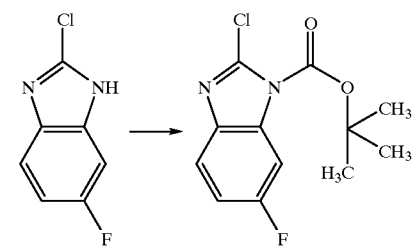

The title compound was prepared by a similar method to Preparation 21 from 2-chloro-6-fluoro-1H-1,3-benzimidazole [see JP 62061978 A2 870318. Showa, and references cited within]. The crude product was purified by column chromatography on silica gel eluting with a solvent gradient of 100:0 changing to 90:10, by volume, hexane-:ethyl acetate to afford tert-butyl 2-chloro-6-fluro-1H-1,3-benzimidazole-1-carboxylate as a white solid, as a 1:1 mixture of regioisomers.

$^1$H-NMR (d$_4$-MeOH)δ: 8.00 (0.5H, m), 7.70 (0.5H, d), 7.60 (0.5H, m), 7.40 (0.5H, d), 7.20 (2H, m), 1.70 (9H, s).

Preparation 23 tert-Butyl 2,6-dichloro-1H-1,3-benzimidazole-1-carboxylate

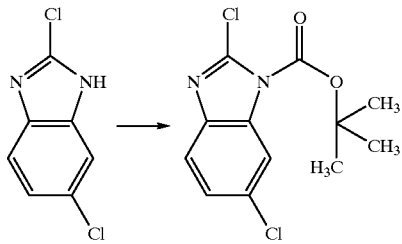

The title compound was prepared by a similar method to Preparation 21 from 2,6-dichloro-1H-1,3-benzimidazole [see US, 44pp. cont.-in-part of U.S. Pat. No. 5,248,672. CODEN:USXXAM, U.S. Pat. No. 5,574,058 A 961112]. The crude product was purified by column chromatography on silica gel eluting with a solvent gradient of 100:0 changing to 80:20, by volume, hexane:ethyl acetate in 5% increments to afford tert-butyl 2,6-dichloro-1H-1,3-benzimidazole-1-carboxylate as a solid, as a 1:1 mixture of regioisomers.

$^1$H-NMR (CDCl$_3$)δ: 8.00 (0.5H, s), 7.95 (0.5H, d), 7.65 (0.5H, s), 7.60 (0.5H, d), 7.40 (1H, t), 1.75 (9H, s).

Preparation 24

5-Iodo-1,3-dihydro-2H-1,3-benzimidazol-2-one

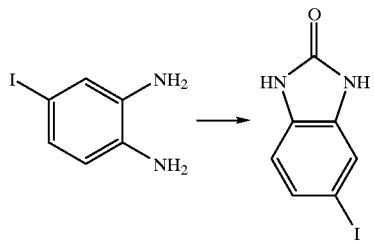

1,1'-Carbonyldiimidazole (13.6 g) was added to a solution of 2-amino-4-iodophenylamine (13.2 g) [see Makromol. Chem. (1993), 194(3), 859–868] in tetrahydrofuran (100 ml). The reaction mixture was stirred for 18 hours at room temperature, after which time the solvent was removed under reduced pressure, and the residue partitioned between 1N aqueous sodium hydroxide and diethyl ether. The aqueous was acidified with concentrated aqueous hydrochloric acid, and the resulting white precipitate filtered off and washed with water to afford 5-iodo-1,3-dihydro-2H-1,3-benzimidazol-2-one (14.0 g) as a white solid.

$^1$H-NMR (d$^6$-DMSO)δ: 10.70 (1H, s), 10.65 (1H, s), 7.25 (1H, d), 7.20 (1H, s), 6.75 (1H, d).

Preparation 25

2-Chloro-6-iodo-1H-1,3-benzimidazole

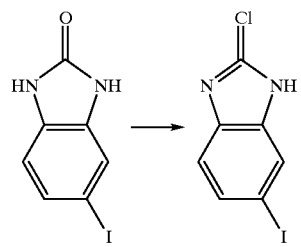

5-Iodo-1,3-dihydro-2H-1,3-benzimidazole-2-one (7 g) [see Preparation 24] was added to a solution of phosphoryl chloride (135 ml). The reaction mixture was then heated to 120° C. and stirred for 2 hours, after which time the phosphoryl chloride was removed under reduced pressure and the residue diluted with water. The residual aqueous solution was neutralised with aqueous potassium hydrogen carbonate solution and the product extracted with 90:10, by volume, dichloromethane:methanol, dried over magnesium sulphate and the solvent removed under reduced pressure to afford 2-chloro-6-iodo-1H-1,3-benzimidazole (3.68 g) as a white solid.

$^1$H-NMR (d$_4$-MeOH) δ: 7.90 (1H, s), 7.60 (1H, d), 7.35 (1H, d).

MS: 279 (MH$^+$).

Preparation 26 tert-Butyl 2-chloro-6-iodo-1H-1,3-benzimidazole-1-carboxylate

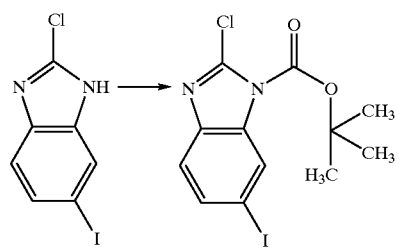

The title compound was prepared by a similar method to Preparation 21 from 2-chloro-6-iodo-1H-1,3-benzimidazole [see Preparation 25]. The crude product was purified by column chromatography on silica gel eluting with a solvent system of 95:5, by volume, hexane:ethyl acetate to afford tert-butyl 2-chloro-6-iodo-1H-1,3-benzimidazole-1-carboxylate as a white solid, as a 1:1 mixture of regioisomers.

$^1$H-NMR (d$_4$-MeOH)δ: 8.35 (0.5H, s), 7.95 (0.5H, s), 7.75 (1.5H, m), 7.40 (0.5H, d), 1.75 (9H, s).

MS: 379 (MH$^+$).

Preparation 27 tert-Butyl 2,5,6-trichloro-1H-1,3-benzimidazole-1-carboxylate

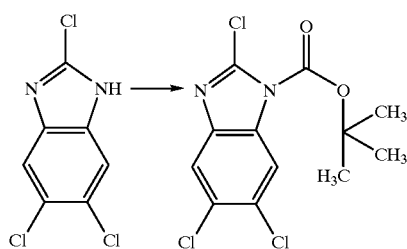

The title compound was prepared by a similar method to Preparation 2,5,6-trichloro-1H-1,3-benzimidazole [see J. Med. Chem. (1995), 4098]. The crude product was purified by column chromatography on silica gel eluting with a solvent gradient of 100:0 changing to 90:10, by volume, hexane:ethyl acetate to afford tert-butyl 2,5,6-trichloro-1H-1,3-benzimidazole-1-carboxylate as a white solid.

$^1$H-NMR (CDCl$_3$)δ: 8.10 (1H, s), 7.80 (1H, s), 1.75 (9H, s).

MS: 321 (MH$^+$).

Preparation 28/Example 36

Benzyl (2S)-1-(5-chloro-1,3-benzoxazol-2-yl)-2-piperidinecarboxylate

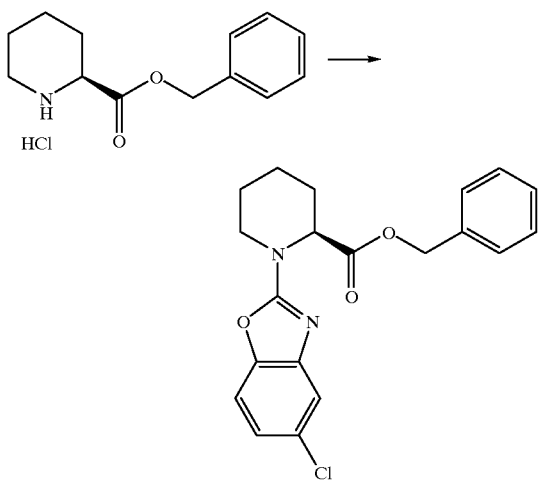

The title compound was prepared by a similar method to Preparation 2 from (2S)-2-[(benzyloxy)carbonyl]piperidinium chloride [see EP 530167 A1 930303] and 2,5-dichloro-1,3-benzoxazole [see J.O.C. (1996), 61(10), 3289–3297]. The crude product was purified by column chromatography on silica gel eluting with a solvent system of 95:5, by volume, hexane:ethyl acetate to afford benzyl (2S)-1-(5-chloro-1,3-benzoaxazol-2-yl)-2-piperidinecarboxylate as an oil.

$^1$H-NMR (CDCl$_3$)δ: 7.30 (6H, m), 7.15 (1H, d), 7.00 (1H, d), 5.30–5.15 (2H, m), 5.05 (1H, d), 4.20 (1H, d), 3.40 (1H, t), 2.40 (1H, d), 1.90–1.50 (3H, m), 1.40–1.20 (2H, m).

MS: 371 (MH$^+$).

Preparation 29

(2S)-1-(5-Chloro-1,3-benzoxazol-2-yl)-2-piperidinecarboxylic acid

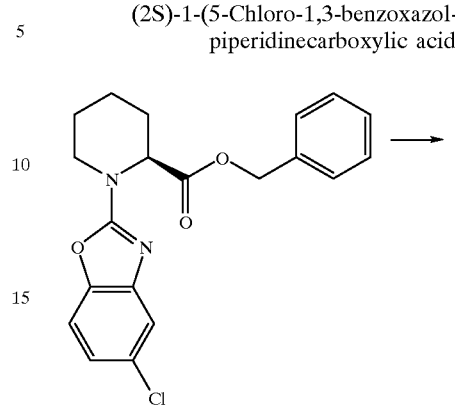

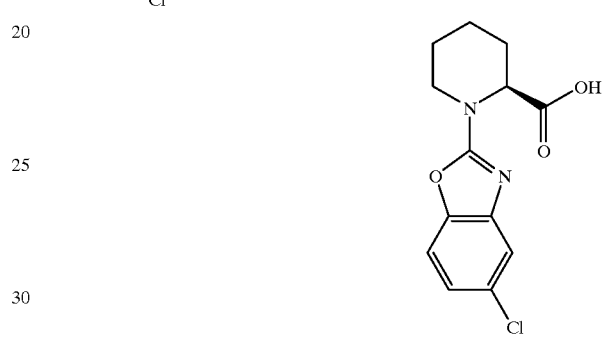

The title compound was prepared by a similar method to Preparation 3 from benzyl (2S)-1-(5-chloro-1,3-benzoxazol-2-yl)-2-piperidinecarboxylate [see Preparation 28] and 1N aqueous lithium hydroxide solution to afford (2S)-1-(5-chloro-1,3-benzoxazol-2-yl)-2-piperidinecarboxylic acid as an oil.

$^1$H-NMR (CDCl$_3$)δ: 8.70 (1H, bs), 7.40 (1H, m), 7.15 (1H, d), 7.00 (1H, d), 5.00 (1H, m), 4.20 (1H, m), 3.40 (1H, t), 2.40 (1H, m), 1.80 (2H, d), 1.60 (1H, m), 1.50 (1H, m), 1.30 (1H, m).

MS: 281 (MH$^+$).

Preparation 30/Example 37

Benzyl (2S)-1-[5-(trifluoromethyl)-1,3-benzoxazol-2-yl]-2-piperidinecarboxylate

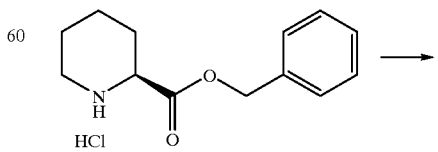

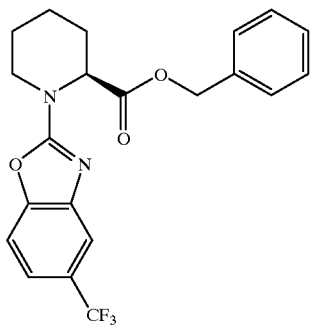

The title compound was prepared by a similar method to Preparation 2 from (2S)-2-[(benzyloxy)carbonyl] piperidinium chloride [see EP 530167 A1 930303] and 2-chloro-5-trifluoromethyl)-1,3-benzoxazole [see J. Med. Chem. (1988), 31, 1719–1728]. The crude product was purified by column chromatography on silica gel eluting with a solvent gradient of 98:2 changing to 90:10, by volume, hexane:ethyl acetate to afford benzyl (2S)-1-[5-(trifluoromethyl)-1,3-benzoaxazol-2-yl]-2-piperidinecarboxylate as an oil.

$^1$H-NMR (CDCl$_3$)δ: 7.60 (1H, s), 7.30 (7H, m), 5.20 (2H, m), 5.15 (1H, d), 4.20 (1H, d), 3.40 (1H, t), 2.40 (1H, d), 1.90–1.30 (5H, m).

MS: 405 (MH$^-$).

Preparation 31

(2S)-1-[5-(Trifluoromethyl)-1,3-benzoxazol-2-yl]-2-piperidinecarboxylic acid

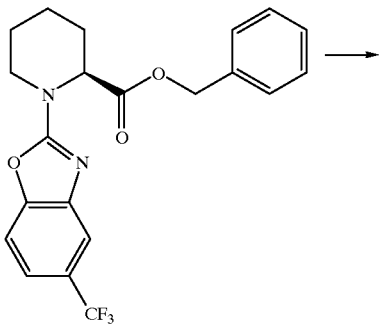

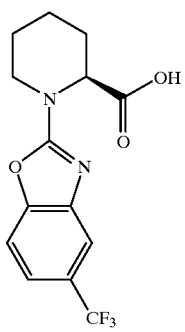

The title compound was prepared by a similar method to Preparation 3 from benzyl (2S)-1-[5-(trifluoromethyl)-1,3-benzoxazol-2-yl]-2-piperidinecarboxylate [see Preparation 30] and 1N aqueous lithium hydroxide solution to afford (2S)-1-[5-(trifluoromethyl)-1,3-benzoxazol-2-yl]-2-piperidinecarboxylic acid as an oil.

$^1$H-NMR (CDCl$_3$)δ: 7.60 (1H, s), 7.40 (1H, d), 7.20 (1H, d), 5.05 (1H, d), 4.25 (1H, d), 3.45 (1H, t), 2.40 (1H, d), 1.90 (3H, m), 1.65 (1H, m), 1.55 (1H, m).

MS: 315 (MH$^+$).

Preparation 32 tert-butyl 2-chloro-1H-benzimidazole-1-carboxylate

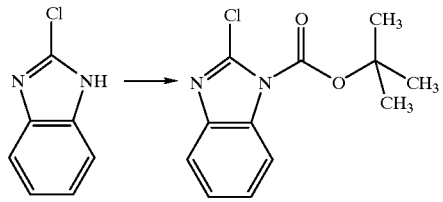

The title compound was prepared by a similar method to Preparation 21 from 2-chlorobenzimidazole and di-t-butyl dicarbonate. The crude product was purified by column chromatography on silica gel eluting with a solvent gradient of 100:0 changing to 90:10, by volume, hexane:ethyl acetate to afford tert-butyl 2-chloro-1H-benzimidizole-1-carboxylate as an oil.

$^1$H-NMR (CDCl$_3$)δ: 7.95 (1H, m), 7.65 (1H, m), 7.35 (2H, m), 1.75 (9H, s).

Preparation 33

2-Sulfanyl-1,3-benzoxazol-6-ol

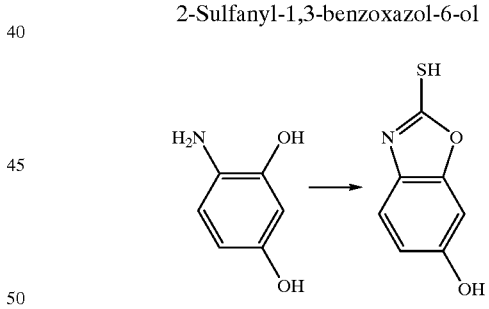

Ground potassium hydroxide (3.13 g) was added to a solution of 2,4-dihydroxyaniline hydrochloride (6.007 g) and ethyl potassium xanthate (17.9 g) in ethanol (100 ml). The reaction mixture was then heated to reflux for 18 hours, after which time the solvent was removed under reduced pressure, the residue dissolved in water and the pH adjusted to 5 with glacial acetic acid. A brown solid formed which was left for 18 hours and then filtered, washed with water and dried to afford 2-sulfanyl-1,3-benzoxazol-6-ol (5.1 g) as a brown solid.

$^1$H-NMR (d$_6$-DMSO)δ: 9.70 (1H, bs), 7.00 (1H, d), 6.85 (1H, s), 6.65 (1H, m).

MS: 168 (MH$^+$).

Preparation 34

2-Chloro-6-hydroxy-1,3-benzoxazole

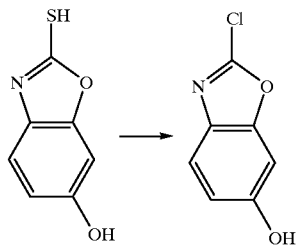

2-Sulfanyl-1,3-benzoxazol-6-ol (2.08 g) [see Preparation 33] was added to thionyl chloride (12.3 ml), followed by dimethylformamide (0.93 ml). The reaction mixture was heated to reflux for 5 minutes, after which time the mixture was allowed to cool. The solvent was removed under reduced pressure, the residue azeotroped twice with xylene, and the residue then partitioned between diethyl ether and water. The organic layer was separated, dried over magnesium sulphate and the solvent removed under reduced pressure. The crude product was purified by column chromatography on silica gel eluting with a solvent gradient of 100:0 changing to 0:100, by volume, hexane:ethyl acetate in 50% increments to afford 2-chloro-1,3-benzoxazol-6-ol (1.715 g) as a white solid.

$^1$H-NMR (d$_6$-DMSO)δ: 9.95 (1H, s), 7.50 (1H, d), 7.05 (1H, s), 6.85 (1H, d).

MS: 168 (MH$^+$).

Preparation 35

2-Chloro-1,3-benzoxazol-6-yl acetate

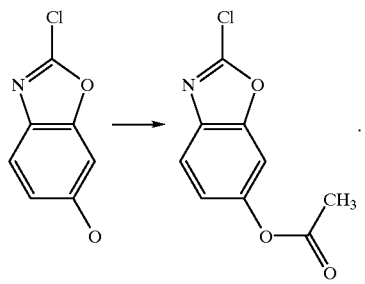

Triethylamine (1.48 ml) was added to a suspension of 2-chloro-1,3-benzoxazol-6-ol (1.63 g) [see Preparation 34] in dichloromethane (20 ml), and after 5 minutes acetic anhydride (1.01 ml) was added. The reaction mixture was stirred at room temperature for 18 hours, after which time the solvent was removed under reduced pressure. The crude product was purified by column chromatography on silica gel eluting with a solvent gradient of 100:0, changing 40:10, changing to 0:100, by volume, hexane:ethyl acetate to afford 2-chloro-1,3-benzoxazol-6-yl acetate (1.63 g) as an oil.

$^1$H-NMR (CDCl$_3$)δ: 7.65 (1H, d), 7.35 (1H, s), 7.10 (1H, d), 2.35 (3H, s).

Preparation 36/Example 38

Benzyl(2S)-1-[6-(acetyloxy)-1,3-benzoxazol-2-yl]-2-piperidinecarboxylate

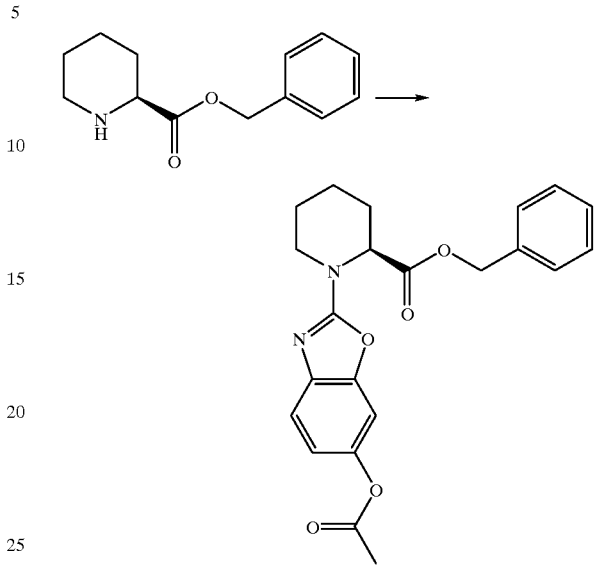

The title compound was prepared by a similar method to Preparation 2 from (2S)-2-[(benzyloxy)carbonyl] piperidinium chloride [see EP 530167 A1 930303] from 2-chloro-1,3-benzoxazol-6-yl acetate [see Preparation 35]. The crude product was purified by column chromatography on silica gel eluting with a solvent gradient of 80:10 changing to 40:10, by volume, hexane:ethyl acetate to afford benzyl (2S)-1-[6-(acetyloxy)-1,3-benzoxazol-2-yl]-2-piperidinecarboxylate as a gum.

$^1$H-NMR (CDCl$_3$) δ: 7.30 (6H, m), 7.05 (1H, s), 6.90 (1H, m), 5.25–5.15 (2H, q), 5.05 (1H, d), 4.20 (1H, d), 3.35 (1H, t), 2.40 (1H, d), 2.35 (3H, s), 1.90–1.2 (5H, m).

M: 395 (MH$^+$).

Rotation: $[\alpha]_D = -136°$ (c=0.1 methanol).

Preparation 37

(2S)-1-[6-(Acetyloxy)-1,3-benzoxazol-2-yl]-2-piperidinecarboxylic acid

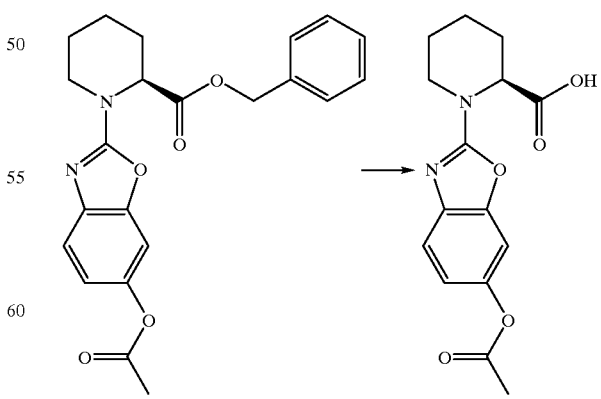

The title compound was prepared by a similar method to Preparation 18 from benzyl (2S)-1-[6-(acetyloxy)-1,3- benzoxazol-2-yl]-2-piperidinecarboxylate [see Preparation 36] to afford (2S)-1-[6-(acetyloxy)-1,3-benzoxazol-2-yl]-2-piperidinecarboxylic acid as a white foam.

¹H-NMR (CDCl₃) δ: 7.35 (1H, d), 7.05 (1H, s), 6.90 (1H, d), 4.95 (1H, d), 4.15 (1H, d), 3.40 (1H, t), 2.45 (1H, d), 2.30 (3H, s), 1.90–1.80 (3H, m), 1.70–1.40 (2H, m).

M: 305 (MH⁺).

Rotation: [α]$_D$=−76.0° (c=0.1 methanol).

Preparation 38/Example 39

2-[(2S)-2-[(2-[(cis)-2,6-Dimethyl-1-piperidinyl]ethylamino)carbonyl]-1-piperidinyl]-1,3-benzoxazol-6-yl acetate

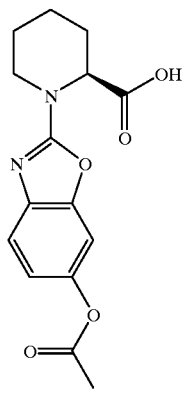

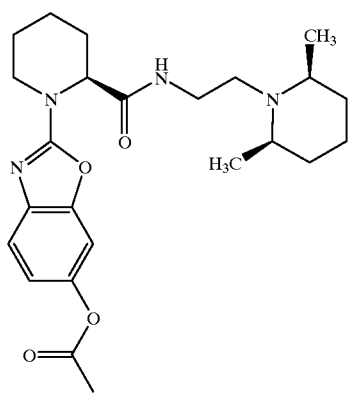

The title compound was prepared by a similar method to Example 1 from (2S)-1-[6-(acetyloxy)-1,3-benzoxazol-2-yl]-2-piperidinecarboxylic acid [see Preparation 37] and 2-[(cis)-2,6-dimethyl-1-piperidinyl]ethylamine [J. Med. Chem, 27(5), (1984), 684–691]. The crude product was purified by column chromatography on silica gel eluting with a solvent gradient of 100:0:0, changing to 99.4:1.4:0.2, by volume, dichloromethane:methanol:0.88 aqueous ammonia solution, to afford 2-[(2S)-2-[(2-[(cis)-2,6-dimethyl-1-piperidinyl]ethylamino)carbonyl]-1-piperidinyl]-1,3-benzoxazol-6-yl acetate as a white foam.

¹H-NMR (CDCl₃) δ: 8.25 (1H, m), 7.10 (1H, d), 6.90 (1H, s), 6.70 (1H, d) 4.80 (1H, m), 4.05 (1H, d), 3.50 (2H, m), 3.30 (1H, t), 3.20–3.00 (4H, bs), 2.25 (1H, d), 2.15 (3H, s), 1.80–1.20 (17H, m).

M: 443 (MH⁺).

Preparation 39/Example 40

(2S)-N-2-[(cis)-2,6-Dimethyl-1-piperidinyl]ethyl-1-(6-hydroxy-1,3-benzoxazol-2-yl)-2-piperidinecarboxamide

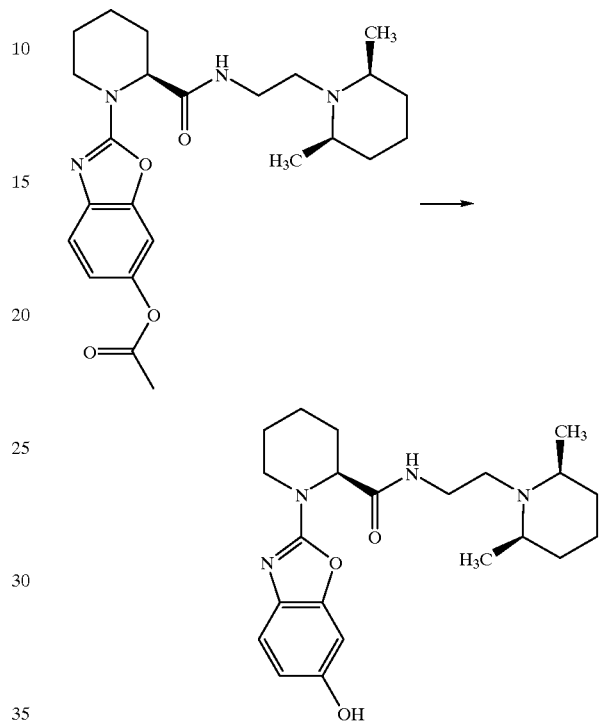

2N Aqueous ammonia solution (10 ml) and acetone (20 ml) were added to 2-[(2S)-2-[(2-[(cis)-2,6-dimethyl-1-piperidinyl]ethylamino)carbonyl]-1-piperidinyl]-1,3-benzoxazol-6-yl acetate (0.389 g) [see Preparation 38] at 0° C. The reaction mixture was then left in a refrigerator for 18 hours, after which time the solvent was removed under reduced pressure. The remaining aqueous layer was washed twice with ethyl acetate, the combined organic layers were then dried over magnesium sulphate and the solvent removed under reduced pressure. The crude product was purified by column chromatography on silica gel eluting with a solvent gradient of 99:1.75:0.25 changing to 97:3.5:0.5, by volume, dichloromethane:methanol:0.88 aqueous ammonia solution to afford (2S)-N-2-[(cis)-2,6-dimethyl-1-piperidinyl]ethyl-1-(6-hydroxy-1,3-benzoxazol-2-yl)-2-piperidinecarboxamide (0.2 g) as a white foam.

¹H-NMR (CDCl₃) δ: 7.15 (1H, d), 6.80 (1H, s), 6.75 (1H, m), 6.65 (1H, d) 4.90 (1H, s), 4.25 (1H, d), 3.40 (1H, m), 3.30–3.20 (2H, m), 2.75 (2H, m), 2.50–2.40 (3H, m), 1.80–1.10 (17H, m).

M: 401 (MH⁺).

Rotation: [α]$_D$=−75.82° c=0.1 methanol).

Preparation 40/Example 41

Methyl(2S)-1-(6-bromo-1,3-benzoxazol-2-yl)-2-piperidinecarboxylate

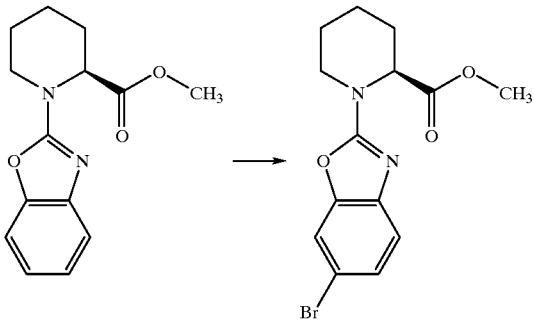

2,4,4,6-Tetrabromo-2,5-cyclohexadien-1-one (4.7 g) was added to a solution of methyl (2S)-1-(1,3-benzoxazol-2-yl)-2-piperidinecarboxylate (3.0 g) [see Preparation 2] in dichloromethane (60 ml) at −10° C. over a period of 10 mins. The reaction mixture was then warmed to room temperature and diluted with dichloromethane. The organic layer was washed with saturated sodium hydrogen carbonate, then with 1N sodium hydroxide solution, dried over sodium sulphate and the solvent removed under reduced pressure to afford methyl (2S)-1-(6-bromo-1,3-benzoxazol-2-yl)-2-piperidinecarboxylate (3.7 g) as a purple coloured oil.

$^1$H-NMR (CDCl$_3$) δ: 7.40 (1H, s), 7.25 (1H, d), 7.20 (1H, d), 5.00 (1H, d), 4.20 (1H, d), 3.80 (3H, s), 3.40 (1H, t), 2.40 (1H, d), 1.80 (3H, m), 1.70 (1H, m), 1.40 (1H, m).

Preparation 41/Example 42

Methyl (2S)-1-(6-isobutyl-1,3-benzoxazol-2-yl)-2-piperidinecarboxylate

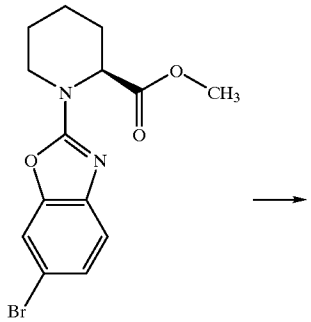

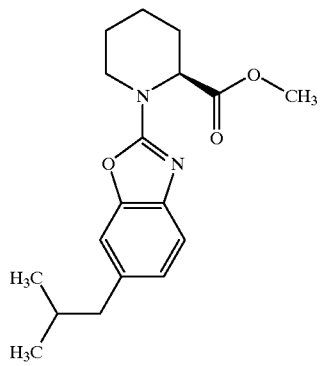

Isobutyl boronic acid (475 mg), potassium carbonate (644 mg) and tetrakis triphenylphosphine palladium (269 mg) were added sequentially to a solution of methyl (2S)-1-(6-bromo-1,3-benzoxazol-2-yl)-2-piperidinecarboxylate (790 mg) [see Preparation 40] in toluene:tetrahydrofuran, 60:40 by volume, (20 ml) under nitrogen. The reaction mixture was then heated to 80° C. for 20 hours, after which time the solvent was removed under reduced pressure and the residue partitioned between water and dichloromethane. The organic layer was separated and washed with water, dried over magnesium sulphate and the solvent removed under reduced pressure. The crude product was purified by column chromatography on silica gel eluting with a solvent system of 80:20, by volume, hexane:ethyl acetate to afford methyl (2S)-1-(6-isobutyl-1,3-benzoxazol-2-yl)-2-piperidinecarboxylate (100 mg) as an oil.

$^1$H-NMR (CDCl$_3$) δ: 7.25 (1H, d), 7.05 (1H, s), 6.95 (1H, d), 5.05 (1H, d), 4.20 (1H, d), 3.75 (3H, s), 3.40 (1H, t), 2.50 (2H, d), 2.35 (1H, d), 1.90–1.80 (4H, m), 1.70–1.60 (1H, m), 1.40 (1H, m), 0.95 (6H, d).

M: 317 (MH$^+$).

Preparation 42

(2S)-1-(6-Isobutyl-1,3-benzoxazol-2-yl)-2-piperidinecarboxylic acid

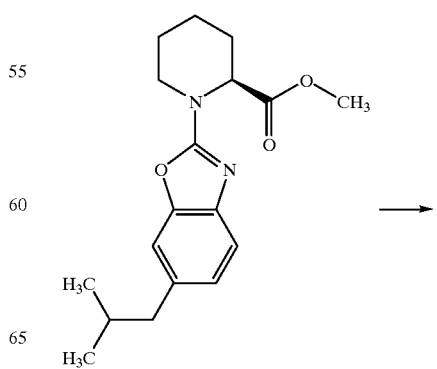

-continued

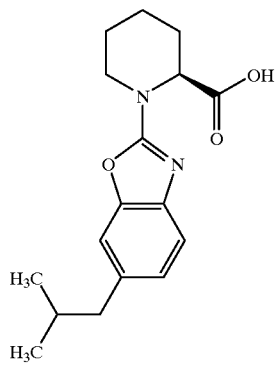

The title compound was prepared by a similar method to Preparation 3 from methyl (2S)-1-(6-isobutyl-1,3-benzoxazol-2-yl)-2-piperidinecarboxylate [see Preparation 41] and 1N aqueous lithium hydroxide solution, to afford (2S)-1-(6-isobutyl-1,3-benzoxazol-2-yl)-2-piperidinecarboxylate acid as a foam.

$^1$H-NMR (CDCl$_3$) δ: 7.30 (1H, m), 7.05 (1H, s), 6.95 (1H, d), 5.05 (1H, m), 4.20 (1H, d), 3.40 (1H, t), 2.50–2.20 (3H, m), 1.85 (4H, m), 1.70–1.40 (2H, m), 0.90 (6H, d).

M: 303 (MH$^+$).

Preparation 43 tert-Butyl 2-chloro-5,6-difluoro-1H-1,3-benzimidazole-1-carboxylate

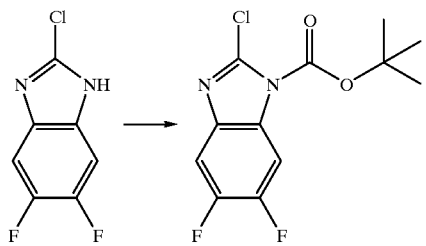

The title compound was prepared by the method of Preparation 21 from 2-chloro-5,6-difluoro-1H-1,3,-benzimidazole [J. Med. Chem. 1997, 40(5), 811].

$^1$H-NMR (d4-MeOH) δ: 7.85 (1H, M), 7.53 (1H, M), 1.71 (9H, s).

Preparation 44 tert-Butyl 2-chloro-5-methyl-1H-1,3-benzimidazole-1-carboxylate

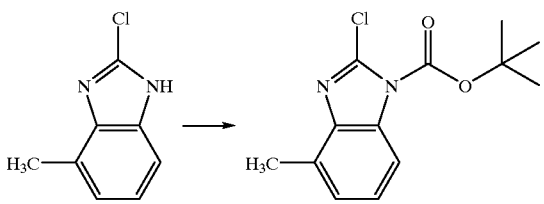

The title compound was prepared by the method of Preparation 21 from 2-chloro-4-methyl-1H-1,3-benzimidazole [WO. 9015058].

$^1$H-NMR (d4-MeOH) δ: 7.74 (1H, d), 7.25 (1H, m), 7.16 (1H, d), 2.60 (3H, s), 1.73 (9H, s).

Preparation 45 tert-Butyl 2-chloro-5-methyl-1H-1,3-benzimidazole-1-carboxylate

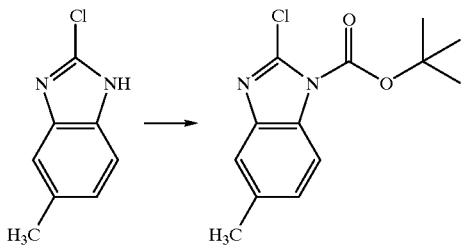

The title compound was prepared by the method of Preparation 21 from 2-chloro-5-methyl-1H-1,3-benzimidazole [G.B. 1015937], affording the title compound as a 1:1 mixture of regioisomers.

$^1$H-NMR (d4-MeOH) δ: 7.78 (1H, m), 7.53 (0.5H, d), 7.42 (0.5H, s), 7.16 (1H, m), 2.49 (1.5H, s), 2.45 (1.5H, s), 1.73 (9H, s).

Preparation 46

4-Fluoro-1,3-dihydro-2H-1,3-benzimidazole-2-one

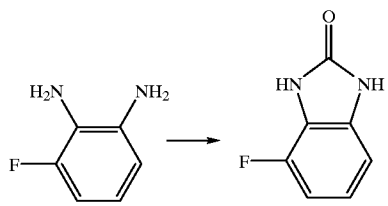

The title compound was prepared by the method of Preparation 24 from 1,2-diamino-3-fluorobenzene [J.O.C. 1969, 34(2), 384] and 1,1'-carbonyldimidazole.

$^1$H-NMR (d4-MeOH) δ: 6.98 (1H, m), 6.84–6.79 (2H, m).

Analysis: Found C, 54.99; H, 3.19; N, 18.19; C$_7$H$_5$FN$_2$O requires C, 55.27; H, 3.31; N, 18.41%.

Preparation 47

2-Chloro 4-fluoro-1H-1,3-benzimidazole

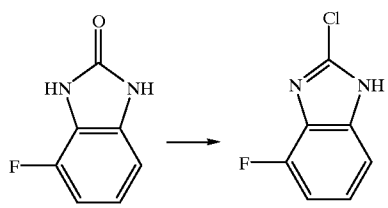

The title compound was prepared by the method of Preparation 25 from 4-fluoro-1,3-dihydro-2H-1,3-benzimidazole-2-one [see Preparation 46].

$^1$H-NMR (d4-MeOH) δ: 7.32 (1H, d), 7.28 (1H, m), 7.00 (1H, t).

Preparation 48 tert-Butyl 2-chloro-4-fluoro-1H-1,3-benzimidazole-1-carboxylate

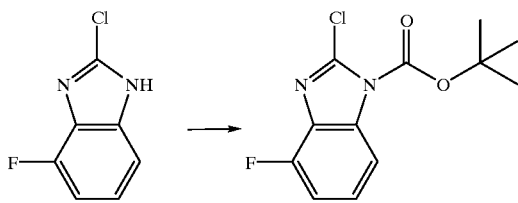

The title compound was prepared by the method of Preparation 21 from 2-chloro-4-fluoro-1H-1,3,-benzimidazole [see Preparation 47].

$^1$H-NMR (d4-MeOH) δ: 7.79 (1H, d), 7.38 (1H, m), 7.12 (1H, t), 1.73 (9H, s).

Preparation 49

2-Sulfanyl-7-(methoxy)carbonyl-1,3-benzoxazole

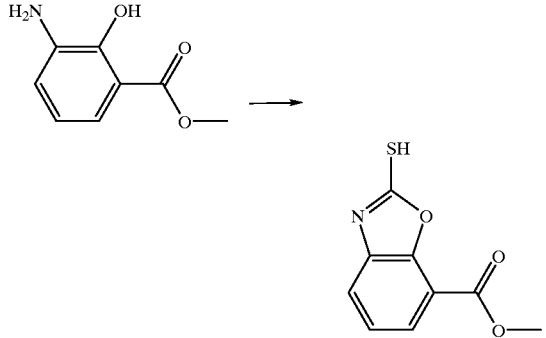

To a solution of methyl 2-hydroxy-3-aminobenzoate (1.81 g) in methanol was added ethyl potassium xanthate (1.91 g) and the mixture heated at reflux for 18 hours. The reaction was cooled, the solvent removed at reduced pressure and the residue dissolved in water. To this solution was added glacial acetic acid and a white precipitate formed which was collected by vacuum filtration. The solid was washed with water and dried to afford 2-sulfanyl-7-(methoxy)carbonyl-1,3-benzoxazole (1.59 g) as a white powder.

$^1$H-NMR (d$_4$-MeOH) δ: 7.80 (1H, d), 7.39 (2H, m), 3.95 (3H, s)

MS: 227.1 (MH$^+$)

Preparation 50/Example 43

Benzyl (2S)-1-[7-(methoxy)carbonyl-1,3-benzoxazol-2-yl]-2-piperidinecarboxylate

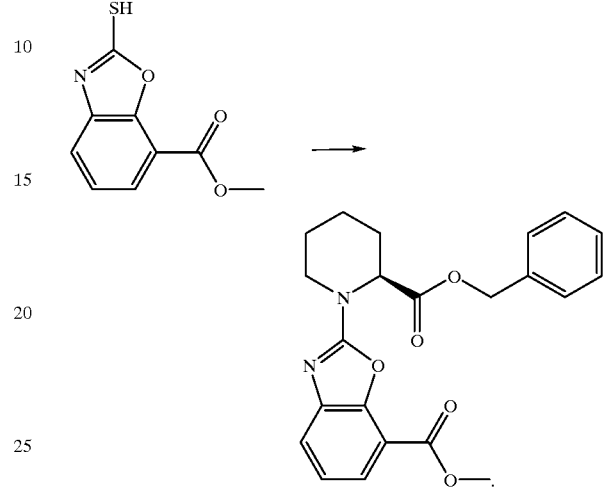

2-Sulfanyl-7-(methoxy)carbonyl-1,3-benzoxazole (1.00 g) [see Preparation 49] was added to thionyl chloride (4.9 ml) followed by dimethylformamide (0.37 ml) and the mixture heated at reflux for 10 minutes. The mixture was cooled and the solvent removed at reduced pressure, the residue was azeotroped twice the xylene to afford a tan solid. This solid was immediately dissolved in acetonitrile (20 ml) and N-ethyldiisopropylamine (3.3 ml) and (2S)-2-[(benzyloxy)carbonyl]piperidinium chloride (1.22 g) was added and the mixture was then heated at reflux for 7 hours. The reaction was cooled, the solvent removed at reduced pressure, and the residue dissolved in ethyl acetate and wash sequentially with 1M aqueous citric acid solution, saturated aqueous sodium hydrogen carbonate solution, brine, then dried over magnesium sulfate and the solvent removed at reduced pressure. The crude product was purified by column chromatography on silica gel eluting with a solvent gradient of 5:1, by volume, hexane:ethyl acetate to afford benzyl (2S)-1-[7-(methoxy)carbonyl-1,3-benzoxazol-2-yl]-2-piperidinecarboxylate (0.44 g) as an orange gum.

$^1$H-NMR (CDCl$_3$) δ: 7.62 (1H, d), 7.55 (1H, d), 7.28 (5H, m), 7.20 (1H, t), 5.25 (2H, m), 5.18 (1H, m), 4.25 (1H, m), 3.92 (3H, s), 3.40 (1H, m), 2.38 (1H, m), 1.90 (3H, m), 1.60 (1H, m), 1.39 (1H, m)

MS: 395.3 (MH$^+$)

Accurate mass measurement: $C_{22}H_{23}N_2O_5$ (MH$^+$) requires 395.1607. Found 395.1610

Preparation 51

(2S)-1-[7-(Methoxy)carbonyl-1,3-benzoxazol-2-yl]-2-piperidinecarboxylic acid

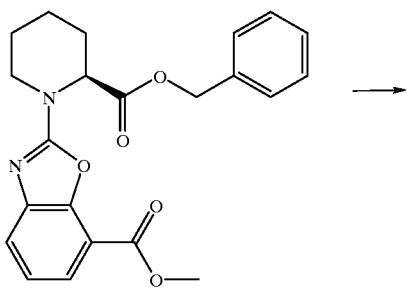

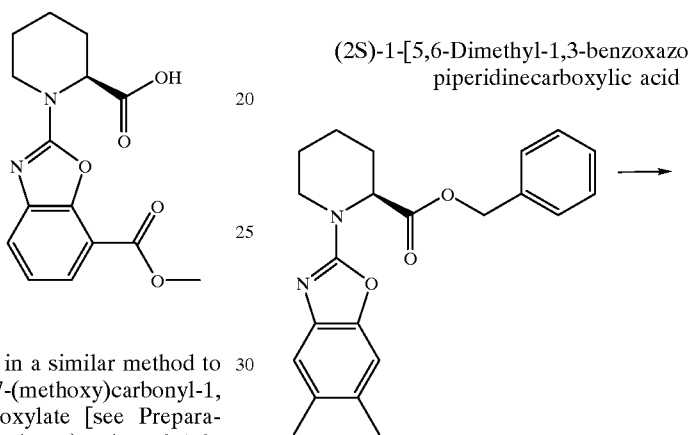

The title compound was prepared in a similar method to Preparation 18 from benzyl (2S)-1-[7-(methoxy)carbonyl-1,3-benzoxazol-2-yl]-2-piperidinecarboxylate [see Preparation 50] to afford (2S)-1-[7-(methoxy)carbonyl-1,3-benzoxazol-2-yl]-2-piperidinecarboxylic acid as a brown gum.

$^1$H NMR ($d_4$-MeOH) δ: 7.59 (1H, d), 7.42 (1H, d), 7.20 (1H, t), 4.80 (1H, m), 4.12 (1H, m), 3.95 (3H, s), 3.55 (1H, m), 2.42 (1H, d), 1.80–1.40 (5H, m)

MS: 304.9 (MH$^+$)

Accurate mass measurement: $C_{15}H_{16}N_2O_5$ (M$^+$) requires 304.1059. Found 304.1064

Preparation 52/Example 44

Benzyl (2S)-1-[5,6-dimethyl-1,3-benzoxazol-2-yl]-2-piperidinecarboxylate

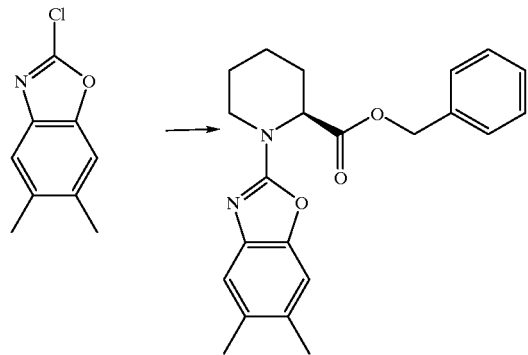

The title compound was prepared by a similar method to Preparation 2 from 2-chloro-5,6-dimethyl-1,3-benzoxazole [see J. Med. Chem. (1972), 15, 523–9] and (2S)-2-[(benzyloxy)carbonyl]piperidine [see EP 530167 A1 930303]. The crude product was purified by column chromatography on silica gel eluting with a solvent gradient of 100:0 changing to 80:20, by volume, hexane:ethyl acetate to afford benzyl (2S)-1-[5,6-dimethyl-1,3-benzoxazol-2-yl]-2-piperidinecarboxylate as a yellow coloured solid.

$^1$H NMR (CDCL$_3$) δ: 7.25 (5H, m), 7.15 (1H, s), 7.00 (1H, s), 5.15 (2H, q), 5.05 (1H, m), 4.15 (1H, d), 3.35 (1H, t), 2.35 (1H, m), 2.25 (6H, s), 1.85 (1H, m), 1.75 (2H, m), 1.60 (1H, m), 1.30 (1H, m).

MS: 365.5 (MH$^+$)

Preparation 53

(2S)-1-[5,6-Dimethyl-1,3-benzoxazol-2-yl]-2-piperidinecarboxylic acid

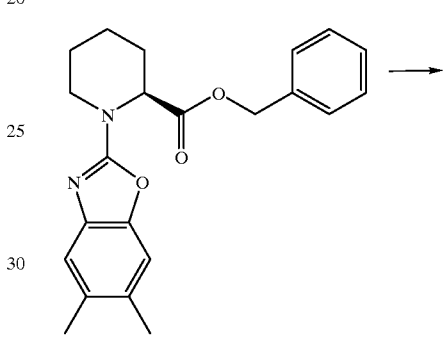

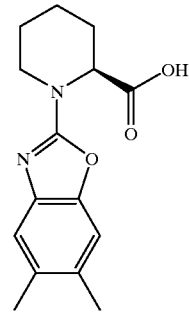

The title compound was prepared by a similar method to Preparation 18 from benzyl (2S)-1-[5,6-dimethyl-1,3-benzoxazol-2-yl]-2-piperidinecarboxylate to afford (2S)-1-[5,6-dimethyl-1,3-benzoxazol-2-yl]-2-piperidinecarboxylic acid as a white foam.

$^1$H NMR (CDCl$_3$) δ: 7.15 (1H, s), 7.00 (1H, s), 4.90 (1H, m), 4.15 (1H, d), 3.40 (1H, t), 2.40 (1H, d), 2.25 (6H, s), 1.80 (3H, m), 1.55 (2H, m).

MS: 275.3 (MH$^+$)

Biological Data

To illustrate the FKBP-inhibiting nature of the substances of the invention, the compounds of Examples 3, 11, 12, 17, 18, 19, 27 and 31 were tested as outlined above vs. FKBP-12 and/or FKBP-52. IC$_{50}$ and K$_{i,app}$ values below 1 μM were observed.

What is claimed is:

1. A compound of the formula (I):

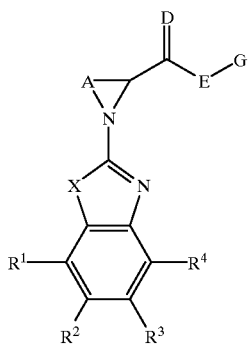

(I)

or a pharmaceutically acceptable salt, or solvate thereof, wherein:

X is O or S;

$R^1$, $R^2$, $R^3$, and $R^4$ are each independently H, OH, OCO($C_{1-6}$ alkyl), $CO_2$($C_{1-6}$ alkyl), $CONH_2$, CONH ($C_{1-6}$ alkyl), CON($C_{1-6}$ alkyl)$_2$, halo, $C_{3-7}$ cycloalkyl, $C_{3-7}$ cycloalkyloxy, $C_{2-6}$ alkenyl, aryl$^1$, $C_{1-6}$ alkyl optionally substituted by one or more substituents selected from halo and $C_{3-7}$ cycloalkyl, and $C_{1-6}$ alkoxy optionally substituted by one or more substituents selected from fluoro and $C_{3-7}$ cycloalkyl;

A is unbranched alkylene of four carbons optionally substituted by up to three $C_{1-6}$ alkyl groups;

D is O or S;

E is NH or N($C_{1-6}$ alkyl);

G is $C_{1-14}$ alkyl or $C_{2-14}$ alkenyl, each of which is optionally substituted by one or more substituents independently selected from halo, aryl, $C_{1-4}$ alkoxy, cycloalk, het and $NR^5R^6$;

$R^5$ and $R^6$ are either each independently H or $C_{1-4}$ alkyl, or are taken together to form, with the nitrogen atom to which they are attached, a 4 to 7-membered heterocyclic ring optionally containing another hetero-moiety selected from $NR^7$, O and $S(O)_p$, and which 4 to 7-membered heterocyclic ring is optionally substituted by up to 3 substituents independently selected from $C_{1-6}$ alkyl and $C_{1-6}$ alkoxy;

$R^7$ is H, $C_{1-6}$ alkyl, $C_{2-6}$ alkenyl, $COR^8$, $SO_2R^8$, $CONR^9R^{10}$, $CO_2R^8$ or $SO_2NR^9R^{10}$;

$R^8$ is $C_{3-7}$ cycloalkyl, $C_{2-6}$ alkenyl, aryl$^1$, or $C_{1-6}$ alkyl optionally substituted by $C_{3-7}$ cycloalkyl or aryl$^1$;

$R^9$ and $R^{10}$ are each independently H, $C_{2-6}$ alkenyl, $C_{3-7}$ cycloalkyl, or $C_{1-6}$ alkyl optionally substituted by $C_{3-7}$ cycloalkyl or aryl;

p is 0, 1, or 2;

wherein "aryl" means phenyl or naphthyl, each of which is optionally substituted by up to 3 substituents independently selected from $C_{1-6}$ alkyl optionally substituted by one or more halo or $C_{3-7}$ cycloalkyl groups, $C_{2-6}$ alkenyl, $C_{1-6}$ alkoxy, $C_{2-6}$ alkenyloxy, OH, halo, $NO_2$, phenyloxy, benzyloxy, phenyl and $NH_2$;

"aryl$^1$" means phenyl, naphthyl or benzyl, each of which is optionally substituted by 1 or 2 substituents independently selected from $C_{1-6}$ alkyl optionally substituted by one or more halo or $C_{3-7}$ cycloalkyl groups, $C_{1-6}$ alkoxy and halo;

"cycloalk" is $C_{3-8}$ cycloalkyl optionally substituted by up to 3 substituents independently selected from $C_{2-6}$ alkenyl, $C_{1-6}$ alkoxy, $C_{2-6}$ alkenyloxy, OH, halo, and $C_{1-6}$ alkyl optionally substituted by one or more halo;

and "het" means a 5- or 6-membered monocyclic, or 8-, 9- or 10-membered bicyclic heterocycle containing 1 to 3 heteroatoms independently selected from O, N and S, which is optionally substituted by up to 3 substituents independently selected from $C_{1-6}$ alkyl optionally substituted by one or more halo or $C_{3-7}$ cycloalkyl groups, $C_{2-6}$ alkenyl, $C_{1-6}$ alkoxy, $C_{2-6}$ alkenyloxy, OH, halo, $NO_2$, phenyloxy, benzyloxy and $NH_2$.

2. A substance according to claim 1 wherein X is O.

3. A substance according to claim 1 wherein at least two of $R^1$, $R^2$, $R^3$ and $R^4$ are H.

4. A substance according to claim 1 wherein $R^1$ is H, halo or $CO_2$($C_{1-6}$ alkyl).

5. A substance according to any previous claim wherein $R^2$ is H, halo, $C_{3-7}$ cycloalkyl, $C_{3-7}$ cycloalkyloxy, $C_{2-6}$ alkenyl, $C_{1-6}$ alkyl optionally substituted by one or more substituents selected from halo and $C_{3-7}$ cycloalkyl, or $C_{1-6}$ alkoxy optionally substituted by one or more substituents selected from fluoro and $C_{3-7}$ cycloalkyl.

6. A substance according to claim 1 wherein $R^3$ is H, halo, $C_{3-7}$ cycloalkyl, $C_{3-7}$ cycloalkyloxy, $C_{2-6}$ alkenyl, $C_{1-6}$ alkyl optionally substituted by one or more substituents selected from halo and $C_{3-7}$ cycloalkyl, or $C_{1-6}$ alkoxy optionally substituted by one or more substituents selected from fluoro and $C_{3-7}$ cycloalkyl.

7. A substance according to claim 1 wherein X is O, or $R^2$ and $R^3$ are independently H, halo or $CF_3$.

8. A substance according to claim 1 wherein $R^4$ is H, halo or $C_{1-6}$ alkyl.

9. A substance according to claim 1 wherein D is O.

10. A substance according to claim 1 wherein E is NH.

11. A substance according to claim 1 wherein G is $C_{1-14}$ alkyl or $C_{2-14}$ alkenyl, each of which is mono- or disubstituted by substituents independently selected from het, aryl, cycloalk or $NR^5R^6$.

12. A substance according to claim 1 wherein the compound has the stereochemistry shown in formula (IB) below

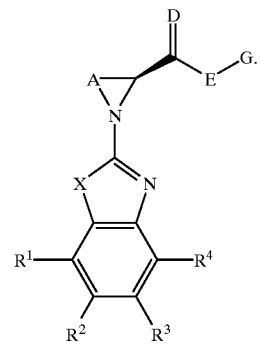

(IB)

13. A substance according to claim 1 wherein $R^1$ is H or $CO_2CH_3$.

14. A substance according to claim 1 wherein $R^2$ is H, halo, $C_{1-6}$ alkyl optionally substituted by one or more substituents selected from halo and $C_{3-7}$ cycloalkyl, or $C_{1-6}$ alkoxy optionally substituted by one or more $C_{3-7}$ cycloalkyl groups.

15. A substance according to claim 1 wherein $R^3$ is H, halo, $C_{1-6}$ alkyl optionally substituted by one or more substituents selected from halo and $C_{3-7}$ cycloalkyl, or $C_{1-6}$ alkoxy optionally substituted by one or more $C_{3-7}$ cycloalkyl groups.

16. A substance according to claim 1 wherein $R^4$ is H or $CH_3$.

17. A substance according to claim 1 wherein G is $C_{2-4}$ alkyl or $C_{2-4}$ alkenyl, each of which is terminally monosubstituted by $NR^5R^6$.

18. A substance according to claim 1 wherein $R^2$ is H, halo, $C_{1-4}$ alkyl optionally substituted by one or more halo, or $C_{1-4}$ alkoxy.

19. A substance according to claim 1 herein $R^3$ is H, halo, $C_{1-4}$ alkyl optionally substituted by one or more halo, or $C_{1-4}$ alkoxy.

20. A substance according to claim 1 wherein G is $C_{2-4}$ alkyl or $C_{2-4}$ alkenyl, each of which is terminally substituted by $NR^5R^6$, where $R^5$ and $R^6$ are either each independently H or $C_{1-6}$ alkyl, or are taken together to form, with the nitrogen atom to which they are attached, a 5 to 7-membered ring optionally containing another hetero-moiety selected from $NR^7$ or O, and which ring is optionally substituted by up to 3 substituents independently selected from $C_{1-6}$ alkyl and $C_{1-6}$ alkoxy, and wherein $R^7$ is H, $C_{1-6}$ alkyl, $COR^8$ or $CONR^9R^{10}$.

21. A substance according to claim 1 wherein $R^2$ is H, F, I, Br, Cl, $CH_3$, $C_2H_5$, $CH_2CH(CH_3)_2$, $CF_3$, $OCH_3$ or $OCH(CH_3)_2$.

22. A substance according to claim 1 wherein $R^3$ is H, F, I, Br, Cl, $CH_3$, $C_2H_5$, $CH_2CH(CH_3)_2$, $CF_3$, $OCH_3$ or $OCH(CH_3)_2$.

23. A substance according to claim 1 wherein G is $(CH_2)_mNR^5R^6$, where m is 2, 3 or 4, and $R^5$ and $R^6$ are either each both H, or are taken together to form, with the nitrogen atom to which they are attached, a 6-membered ring optionally containing another hetero-moiety at the 4-position relative to the ring nitrogen directly attached to the $(CH_2)_m$ moiety, which hetero-moiety is selected from NH, $NCOCH_3$, $NCH_3$, $NCONHCH(CH_3)_2$ or O, and which ring is optionally substituted by up to 2 $CH_3$ substituents on the ring atoms adjacent to the ring nitrogen directly attached to the $(CH_2)_m$ moiety.

24. A substance according to claim 1 wherein $R^2$ is H, F, Cl, Br, I or $CF_3$.

25. A substance according to claim 1 wherein $R^3$ is H, F, Cl, Br, I or $CF_3$.

26. A substance according to claim 1 wherein G is $(CH_2)_2NR^5R^6$, where $R^5$ and $R^6$ are both H or are taken together taken together to form, with the nitrogen atom to which they are attached, a 6-membered ring optionally containing another hetero-moiety at the 4-position relative to the ring nitrogen directly attached to the $(CH_2)_m$ moiety, which hetero-moiety is selected from NH, $NCOCH_3$, $NCH_3$, $NCONHCH(CH_3)_2$ or O, and which ring is optionally substituted by up to 2 $CH_3$ substituents on the ring atoms adjacent to the ring nitrogen directly attached to the $(CH_2)_2$ moiety.

27. A substance according to claim 1 wherein G is $(CH_2)_2NR^5R^6$, where $NR^5R^6$ is piperidino, morpholino, piperazino,

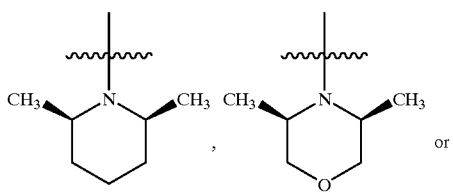

or

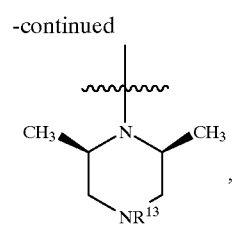

where $R^{13}$ is H, $COCH_3$, $CH_3$, or $CONHCH(CH_3)_2$.

28. A substance according to claim 1 selected from the compounds:

(2S)-1-(1,3-benzoxazol-2-yl)-$N^2$-(2-piperidineoethyl)-2-piperidinecarboxamide;

(2S)-$N^2$-(2-aminoethyl)-1-(1,3-benzoxazol-2-yl)-2-piperidinecarboxamide;

(2S)-1-(1,3-benzoxazol-2-yl)-$N^2$-2-[(cis)-2,6-dimethyl-1-piperidinyl]ethyl-2 piperidinecarboxamide;

(2S)-1-(5-methyl-1,3-benzoxazol-2-yl)-$N^2$-(2-piperidineoethyl)-2-piperidinecarboxamide;

(2S)-1 (5-chloro-1,3-benzoxazol-2-yl)-$N^2$-(2-piperidineoethyl)-2-piperidinecarboxamide;

(2S)-1-(5-trifluoromethyl-1,3-benzoxazol-2-yl)-$N^2$-(2-piperidineoethyl)-2-piperidinecarboxamide;

(2S)-1-(6-(2-methylpropyl)-1,3-benzoxazol-2-yl)-$N^2$-(2-piperidineoethyl)-2-piperidinecarboxamide;

(2S)-1-(1,3-benzoxazol-2-yl-$N^2$-2-[(cis)-2,6-dimethyl-1-piperazinyl]ethyl-2-piperidinecarboxamide;

(2S)-$N^2$-2-[(cis)-4-acetyl-2,6-dimethyl-1-piperazinyl]ethyl-1-(1,3 benzoxazol-2-yl)-2-piperidinecarboxamide;

(2S)-1-(1,3-benzoxazol-2-yl)-$N^2$-2 [(cis)-2,4,6-trimethyl-1-piperazinyl]ethyl-2-piperidinecarboxamide;

(cis)-4-[2-([(2S)-1-(1,3-benzoxazol-2-yl)-2-piperidinyl]carbonylamino)ethyl]-$N^1$-isopropyl-3,4-dimethyl-1-piperazinecarboxamide;

(2S)-1-(1,3-benzoxazol-2-yl)-$N^2$-[2-(3,5-dimethylmorpholino)ethyl]-2-piperidinecarboxamide;

(2S)-$N^2$-3-[(cis)-2,6-dimethyl-1-piperidinyl]propyl-1-(5-methyl-1,3-benzoxazol-2-yl)-2-piperidinecarboxamide;

(2S)-1-(1,3-benzoxazol 2-yl)-$N^2$-4-[(cis)-2,6-dimethyl-1-piperidinyl]butyl-2-piperidinecarboxamide;

(2S)-$N^2$-2-[(cis)-2,6-dimethyl-1-piperidinyl]ethyl-1-(5-fluoro-1,3-benzoxazol-2-yl)-2-piperidinecarboxamide;

(2S)-$N^2$-2-[(cis)-2,6-dimethylcyclohexyl]ethyl-1-(5-methoxy-1,3-benzoxazol-2-yl)-2-piperidinecarboxamide;

(2S)-$N^2$-2-[(cis)-2,6-dimethylcyclohexyl]ethyl-1-(5 ethyl-1,3-benzoxazol-2-yl)-2-piperidinecarboxamide;

(2S)-$N^2$-2-[(cis)-2,6-dimethyl-piperidinyl]ethyl-1-(6-isopropoxy-1,3-benzoxazol-2-yl)-2-piperidinecarboxamide;

(2S)-$N^2$-2-[(cis)-2,6-dimethyl-1-piperidinyl]ethyl-1-[7-(methoxy)carbonyl-1,3-benzoxazol-2-yl]-2-piperidinecarboxamide;

(2S)-$N^2$-2[(cis)-2,6-dimethyl-1-piperidinyl]ethyl-1-[5,6-dimethyl-1,3-benzoxazol-2-yl]-2-piperidinecarboxamide;

tert-butyl(cis)-4-[2-([2S)-1(1,3-benzoxazol-2-yl)-2-piperidinyl]carbonylamino)ethyl]-3,5-dimethyl-1-piperazinecarboxylate;

2-[(2S)-2 [(cis)-2,6-dimethyl-1-piperidinyl]ethylamino)carbonyl-1-piperidinyl]-1,3-benzoxazol-6-yl acetate; and (2S)-N-2-[(cis)-2,6-dimethyl-1-piperidinyl]ethyl-1-(6-hydroxy-1,3-benzoxazol-2-yl)-2-piperidinecarboxamide; and pharmaceutically acceptable salts and solvates of said compounds.

29. A substance according to claim 1 selected from the compounds:

(2S)-1-(1,3-benzoxazol-2-yl)-$N^2$-2[(cis)-2,6-dimethyl-1-piperidinyl]ethyl-2-piperidinecarboxamide;

(2S)-1-(1,3-benzoxazol-2-yl)-$N^2$-2-[(cis)-2,4,6-trimethyl 1-piperazinyl]ethyl-2-piperidinecarboxamide;

(cis)-4-[2-([[(2S)-1-(1,3-benzoxazol-2-yl)-2-piperidinyl]carbonylamino)ethyl]-$N^1$-isopropyl-3,4-dimethyl-1-piperazinecarboxamide;

(2S)-1-(1,3-benzoxazol-2-yl)-$N^2$-[2-(3,5-dimethylmorpholino)ethyl]-2-piperidinecarboxamide; and (2S)-$N^2$-2[(cis)-2,6-dimethyl-1-piperidinyl]ethyl-1-[5,6-dimethyl-1,3-benzoxazol-2-yl]-2-piperidinecarboxamide;

and pharmaceutically acceptable salts and solvents of said compounds.

* * * * *